US010722592B2

(12) United States Patent
Lewis et al.

(10) Patent No.: US 10,722,592 B2
(45) Date of Patent: Jul. 28, 2020

(54) CD48 ANTIBODIES AND CONJUGATES THEREOF

(71) Applicant: SEATTLE GENETICS, INC., Bothell, WA (US)

(72) Inventors: Timothy Lewis, Kenmore, WA (US); Kristine Gordon, Hayward, CA (US); Lori Westendorf, Snohomish, WA (US)

(73) Assignee: Seattle Genetics, Inc., Bothell, WA (US)

( * ) Notice: Subject to any disclaimer, the term of this patent is extended or adjusted under 35 U.S.C. 154(b) by 155 days.

(21) Appl. No.: 15/557,910

(22) PCT Filed: Mar. 17, 2016

(86) PCT No.: PCT/US2016/022943
§ 371 (c)(1),
(2) Date: Sep. 13, 2017

(87) PCT Pub. No.: WO2016/149535
PCT Pub. Date: Sep. 22, 2016

(65) Prior Publication Data
US 2018/0092984 A1 Apr. 5, 2018

Related U.S. Application Data

(60) Provisional application No. 62/134,981, filed on Mar. 18, 2015.

(51) Int. Cl.
| *A61K 47/68* | (2017.01) |
| *C07K 16/28* | (2006.01) |
| *C07K 5/02* | (2006.01) |
| *A61K 39/395* | (2006.01) |
| *A61K 39/00* | (2006.01) |

(52) U.S. Cl.
CPC .... *A61K 47/6803* (2017.08); *A61K 39/39566* (2013.01); *A61K 47/6807* (2017.08); *A61K 47/6849* (2017.08); *A61K 47/6883* (2017.08); *C07K 5/0205* (2013.01); *C07K 16/2803* (2013.01); *A61K 2039/505* (2013.01); *C07K 2317/24* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 2005/0260213 A1 | 11/2005 | Koenig et al. |
| 2007/0178072 A1 | 8/2007 | Watanabe |
| 2009/0280116 A1 | 11/2009 | Smith et al. |
| 2012/0076790 A1 | 3/2012 | Classon et al. |
| 2013/0266579 A1 | 10/2013 | Wei et al. |
| 2013/0333061 A1 | 12/2013 | Wu et al. |

FOREIGN PATENT DOCUMENTS

| EP | 1749538 A1 | 2/2007 |
| EP | 2418222 A1 | 2/2012 |

(Continued)

OTHER PUBLICATIONS

PCT Application No. PCT/US2016/022943, Search Report and Written Opinion dated Jun. 23, 2016, 14 pages.

(Continued)

*Primary Examiner* — Karl J Puttlitz
(74) *Attorney, Agent, or Firm* — Seattle Genetics, Inc.

(57) ABSTRACT

The invention provides murine, chimeric, and humanized antibodies that specifically bind to CD48 and conjugates thereof.

55 Claims, 11 Drawing Sheets

Specification includes a Sequence Listing.

```
                         10        20        30        40        50        60
                    ....|....|....|....|....|....|....|....|....|....|....|....|....
mMEM102 vH          .I......P......ET..I..........DFG..........K..........F..E.S.GNV.K...AL
hIGVH7-4-1/JH5      QVQLVQSGSELKKPGASVKVSCKASGYTFTSYAMNWVRQAPGQGLEWMGWINTNTGNPTYAQGFTGRFVF
hMEM102 vHA         ...............................DFG.....................F..E.S.GNV.K.....
hMEM102 vHB         .I.............................DFG.....................F..E.S.GNV.K....L
hMEM102 vHC         .I.............................DFG.....................F..E.S.GNV.K....L 70        80        90        100       110
                    |....|....|......|....|....|....|......|....|...
mMEM102 vH          ..E..AT......NN..S....T.F...RHGNG.V........TL....
hIGVH7-4-1/JH5      SLDTSVSTAYLQISSLKAEDTAVYYCAR-----NWFDSWGQGTLVTVSS
hMEM102 vHA         ............................RHGNG.V.............
hMEM102 vHB         ............................RHGNG.V.............
hMEM102 vHC         ......T.................F...RHGNG.V.............
```

(56) References Cited

FOREIGN PATENT DOCUMENTS

| WO | WO97/35614 A1 | 10/1997 |
| WO | WO2007/011968 A2 | 1/2007 |
| WO | WO2013/173337 A2 | 11/2013 |
| WO | WO2015/057699 A2 | 4/2015 |

OTHER PUBLICATIONS

Bandeira, et al. "Automated de novo protein sequencing of monoclonal antibodies", Nature Biotechnology, vol. 26, No. 12, pp. 1336-1338, (Dec. 2008).

Burke, et al., "Abstract 1786: Development and pharmacological properties of PEGylated glucuronide-auristatin linkers", Proceedings: AACR Annual Meeting 2014, Apr. 5-9; San Diego, CA, AACR; Cancer Res 74, Suppl 19, Abstract No. 1786, (2014).

Burke, et al., "Optimization of a PEGylated GlucuronideMonomethylauristatin E Linker for Antibody-Drug Conjugates", Molecular Cancer Therapeutics, 16(1), pp. 116-123, (Jan. 2017).

EP Application No. 16765773.3, Extended European Search Report, 20 pages, (dated Aug. 3, 2018).

Lyon, et al., "Self-hydrolyzing maleimides improve the stability and pharmacological properties of antibody-drug conjugates", Nature Biotechnology, vol. 32, No. 10, pp. 1059-1062, (Oct. 2014).

ClinicalTrials.gov, "A Safety Study of SGN-CD48A in Patients With Multiple Myeloma", 9 pages, Available at: https://clinicaltrials.gov/ct2/show/NCT03379584?term=cd48a&draw=2&rank=1, 7 pages, (Sep. 18, 2019).

FIGURE 1

```
                      10         20         30         40         50         60
                      |....|....|....|....|....|....|....|....|....|....|....|....|
mMEM102 vH            ....I.....P....ET..I.......DFG.........K........F..E.S.GNV.K...AL
hIGVH7-4-1/JH5        QVQLVQSGSELKKPGASVKVSCKASGYTFTTSYAMNWVRQAPGQGLEWMGWINTNTGNPTYAQGFTGRFVF
hMEM102 vHA           ..I.......................DFG.....................F..E.S.GNV.K....L
hMEM102 vHB           ..........................DFG.....................F..E.S.GNV.K....L
hMEM102 vHC           ..I.......................DFG.....................F..E.S.GNV.K....L 70         80         90         100        110
                      |....|....|....|....|....|....|....|....|....|....|
mMEM102 vH            ..E..AT.....NN..S....T.F..RHGNG.V........TL......
hIGVH7-4-1/JH5        SLDTSVSTAYLQISSLKAEDTAVYYCAR----NWFDSWGQGTLVTVSS
hMEM102 vHA           ...........................RHGNG.V..............
hMEM102 vHB           ...........................RHGNG.V..............
hMEM102 vHC           ......T...............F....RHGNG.V..............
```

CD48 ANTIBODIES AND CONJUGATES THEREOF

CROSS-REFERENCES TO RELATED APPLICATIONS

This application is a U.S. national stage filing under 35 U.S.C. 371 of International Application No. PCT/US2016/022943, filed Mar. 17, 2016, which claims the benefit of U.S. Provisional Patent Application No. 62/134,981, filed Mar. 18, 2015, which is incorporated herein by reference in its entirety.

REFERENCE TO A SEQUENCE LISTING

This application includes an electronic sequence listing in a file named 4000-00111US_Sequence Listing_ST25.txt, created on Aug. 21, 2017 and containing 14 KB, which is hereby incorporated by reference.

FIELD OF THE INVENTION

The invention provides murine, chimeric, and humanized antibodies that specifically bind to CD48 and conjugates thereof.

BACKGROUND OF THE INVENTION

CD48 antigen (Cluster of Differentiation 48) is also known as B-lymphocyte activation marker (BLAST-1) or signaling lymphocytic activation molecule 2 (SLAMF2). CD48 is a member of the CD2 subfamily of the immunoglobulin superfamily (IgSF) which includes SLAM (signaling lymphocyte activation molecules) proteins, such as CD84, CD150, CD229 and CD244. CD48 is found on the surface of lymphocytes and other immune cells, and dendritic cells, and participates in activation and differentiation pathways in these cells. CD48 is known to be expressed on multiple myeloma cells and other cancers of B cell origin, e.g., non-Hodgkins lymphoma (NHL), Chronic lymphocytic leukemia (CLL), Monoclonal Gammopathy of Unknown Significance (MGUS), Waldenstrom's Macroglobulinemia (WM), Primary/Systemic Amyloidosis patient tumor cells, and follicular lymphoma (FL).

BRIEF SUMMARY OF THE INVENTION

In one aspect this disclosure provides a chimeric or humanized antibody that specifically binds to the human CD48 protein. The antibody includes heavy chain CDR sequences of SEQ ID NOs:3-5 and light chain CDR sequences of SEQ ID NOs:6-8. The antibody exhibits higher binding affinity to the human CD48 protein, as compared to a murine antibody that specifically binds to the human CD48 protein and also includes the heavy chain CDR sequences of SEQ ID NOs:3-5 and light chain CDR sequences of SEQ ID NOs:6-8. In one embodiment, the chimeric or humanized antibody exhibits at least 2-fold higher binding affinity for the human CD48 protein, as compared to the murine antibody. In another embodiment, the antibody is a humanized antibody. In a further embodiment, the antibody includes the heavy chain variable region of SEQ ID NO:1. In another embodiment, the antibody includes the light chain variable region of SEQ ID NO:2. In a further embodiment, the antibody includes the heavy chain variable region of SEQ ID NO:1 and the light chain variable region of SEQ ID NO:2. In one embodiment, the antibody is conjugated to a cytotoxic drug attached to a linker.

In a further embodiment, the drug-linker attached to the antibody has the formula:

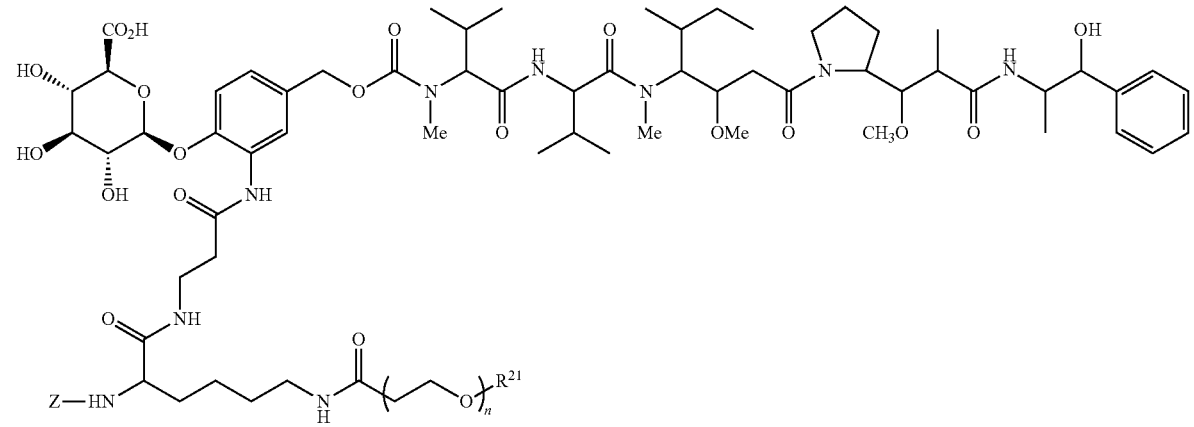

or a pharmaceutically acceptable salt thereof wherein Z represents an organic moiety having a reactive site capable of reacting with a functional group on the antibody to form a covalent attachment thereto, n ranges from 8 to 36, $R^{PR}$ is hydrogen or a protecting group, $R^{21}$ is a capping unit for the polyethylene glycol moiety.

In another aspect, this disclosure provides a humanized antibody that specifically binds to the human CD48 protein, that includes a heavy chain variable region of SEQ ID NO:1 and a light chain variable region of SEQ ID NO:2.

The antibody, in one embodiment, is conjugated to a cytotoxic drug attached to a linker. An exemplary drug-linker has the formula:

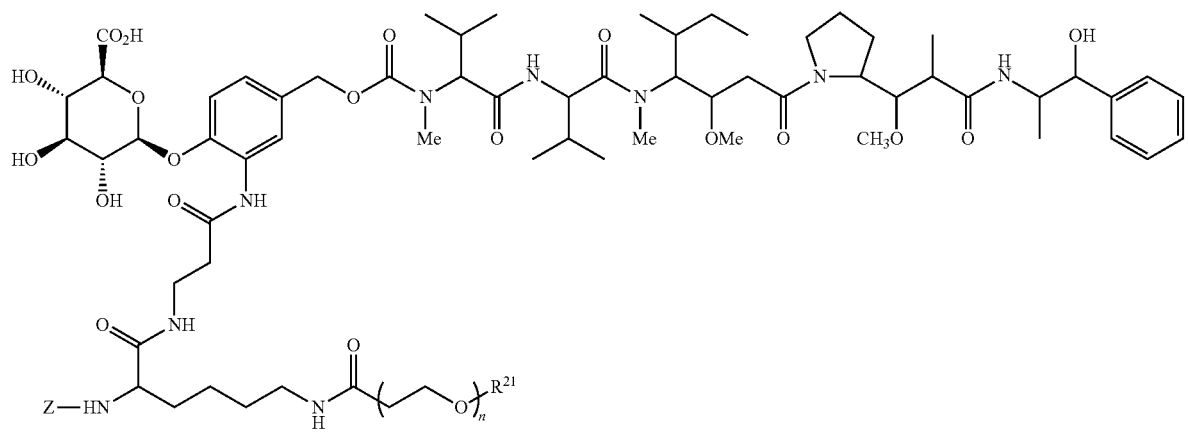

or a pharmaceutically acceptable salt thereof wherein Z represents an organic moiety having a reactive site capable of reacting with a functional group on the antibody to form a covalent attachment thereto, n ranges from 8 to 36, $R^{PR}$ is hydrogen or a protecting group, $R^{21}$ is a capping unit for the polyethylene glycol moiety.

Another exemplary drug-linker for conjugation to the disclosed antibodies has the formula:

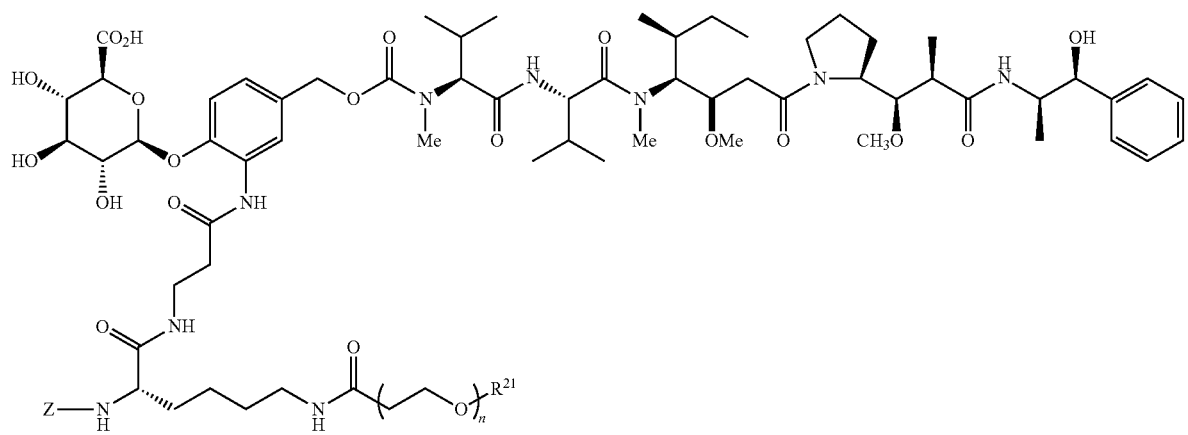

or a pharmaceutically acceptable salt thereof wherein Z represents an organic moiety having a reactive site capable of reacting with a functional group on the antibody to form a covalent attachment thereto, n ranges from 8 to 36, $R^{PR}$ is hydrogen or a protecting group, $R^{21}$ is a capping unit for the polyethylene glycol moiety.

Another exemplary drug-linker for conjugation to the disclosed antibodies has the formula

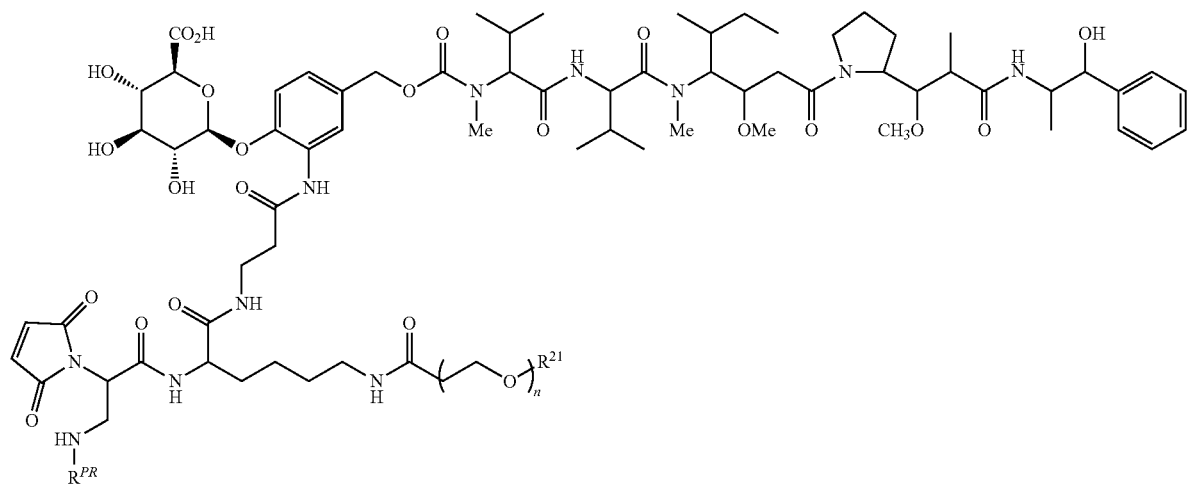

or a pharmaceutically acceptable salt thereof wherein, n ranges from 8 to 36, $R^{PR}$ is hydrogen or a protecting group, $R^{21}$ is a capping unit for the polyethylene glycol moiety. Another exemplary drug-linker for conjugation to the disclosed antibodies has the formula

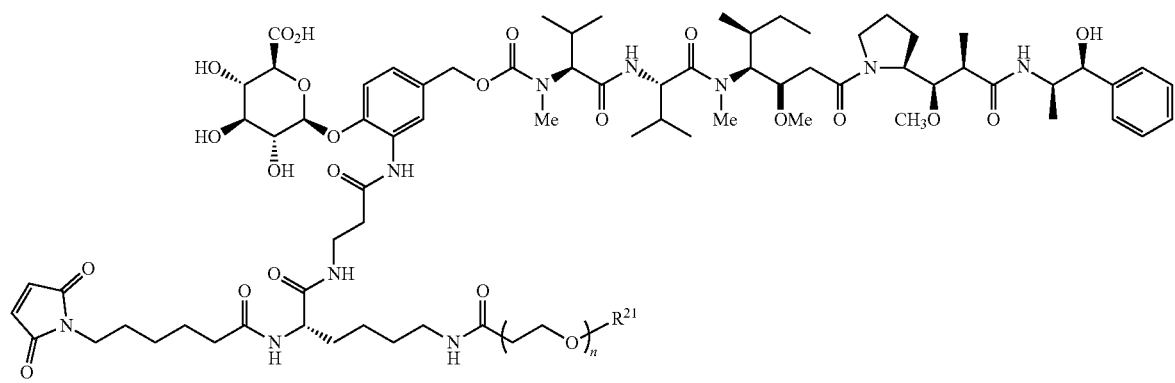

or a pharmaceutically acceptable salt thereof wherein, n ranges from 8 to 36, $R^{PR}$ is hydrogen or a protecting group, $R^{21}$ is a capping unit for the polyethylene glycol moiety. In some embodiments of this disclosure, the value n can range from 8 to 14. In other embodiment of this disclosure, the value n ranges from 10 to 12. In a further embodiment of this disclosure, the value of n is 12. In another embodiment, $R^{21}$ is —$CH_3$ or —$CH_2CH_2CO_2H$.

In another aspect this disclosure provides an anti-CD48 antibody-drug conjugate compound having the formula

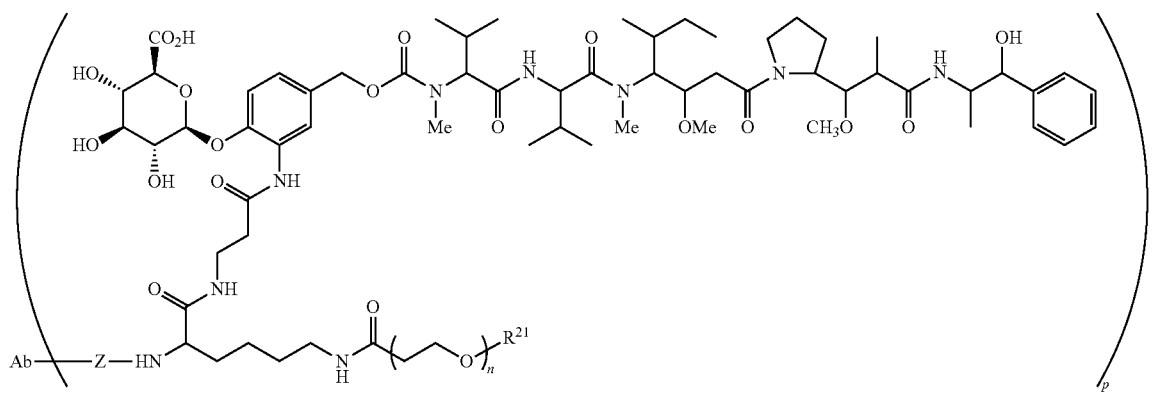

or a pharmaceutically acceptable salt thereof, Z represents an organic moiety linking the antibody and the remainder of the drug-linker via covalent bonds, n ranges from 8 to 36, $R^{21}$ is a capping unit for the polyethylene glycol moiety, and p is from 1 to 16. The antibody can be any of the disclosed anti-CD48 antibodies. In a preferred embodiment, the antibody has the heavy chain variable region of SEQ ID NO:1 and the light chain variable region of SEQ ID NO:2.

Another exemplary drug-linker for conjugation to the disclosed antibodies has the formula:

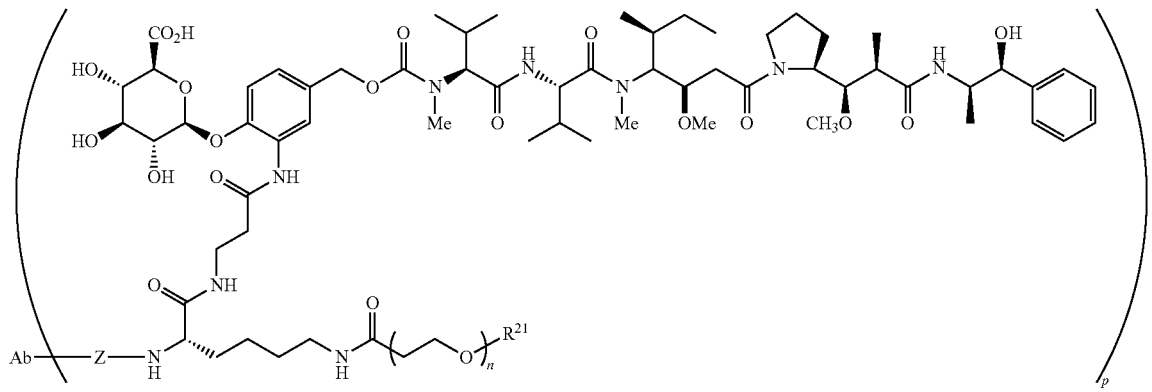

or a pharmaceutically acceptable salt thereof.

Another exemplary drug-linker for conjugation to the disclosed antibodies has the formula:

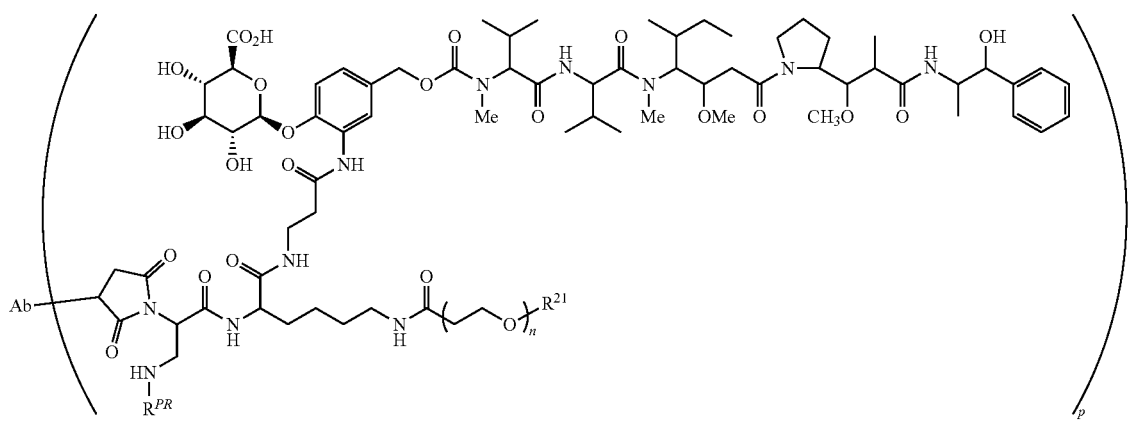

or a pharmaceutically acceptable salt thereof wherein $R^{PR}$ is hydrogen or a protecting group.

Another exemplary drug-linker for conjugation to the disclosed antibodies has the formula:

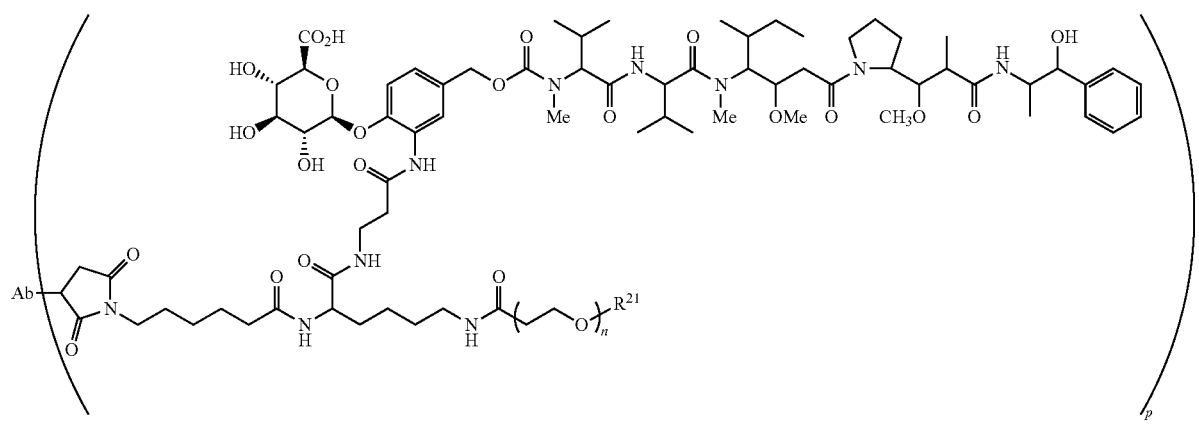
or a pharmaceutically acceptable salt thereof.
Another exemplary drug-linker for conjugation to the disclosed antibodies has the formula:
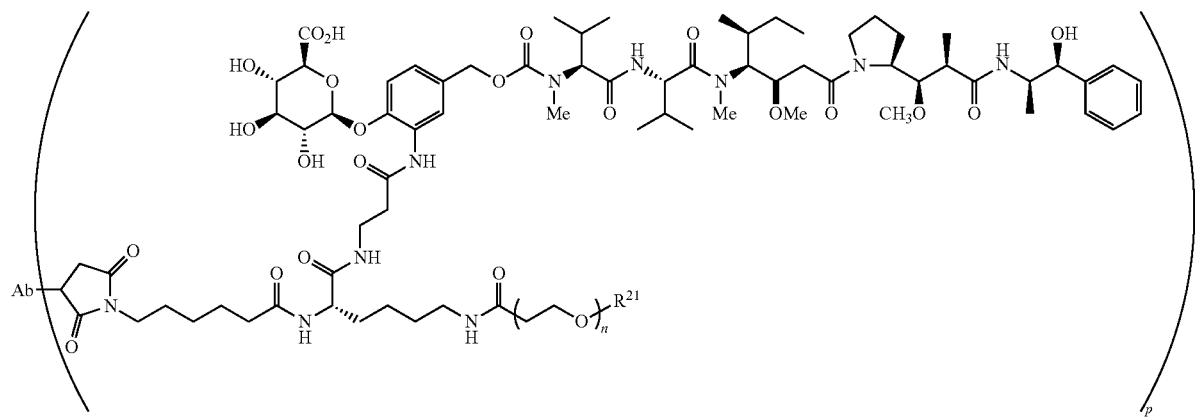
or a pharmaceutically acceptable salt thereof.
Another exemplary drug-linker for conjugation to the disclosed antibodies has the formula:
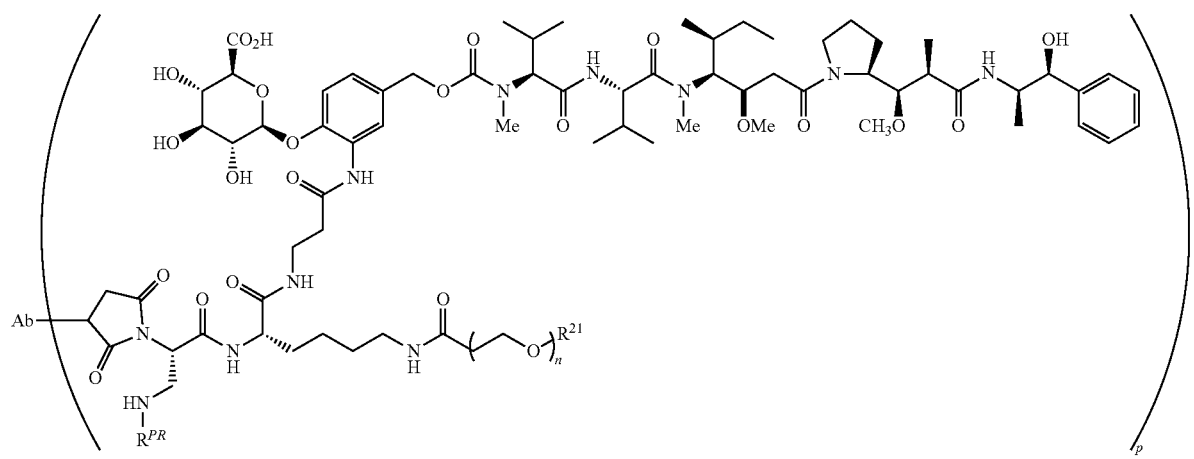

or a pharmaceutically acceptable salt thereof wherein $R^{PR}$ is hydrogen or a protecting group.

In some embodiments of this disclosure, the value n can range from 8 to 14. In other embodiment of this disclosure, the value n ranges from 10 to 12. In a further embodiment of this disclosure, the value of n is 12. In another embodiment, $R^{21}$ is —CH$_3$ or —CH$_2$CH$_2$CO$_2$H.

In another embodiment, any of the disclosed antibody-drug conjugates has a p value of 8. In another embodiment, the drug-linker is attached to the antibody via the cysteine residues of the interchain disulfide bonds of the antibody.

In another embodiment, the antibody-drug conjugate composition includes a population of anti-CD48 antibody-drug conjugate molecules with an average drug load of 8 and with the predominant drug load in the composition being 8.

In another aspect this disclosure provides pharmaceutical compositions and formulations that include the CD48 antibody-drug conjugate disclosed herein.

In a further aspect, the CD48 antibody-drug conjugates are used to treat patients with a cancer that expresses CD48. The CD48 expressing cancer, in one embodiment, is multiple myeloma. In other embodiments, the CD48 expressing cancer is a B cell malignancy, e.g., non-hodgkins lymphoma, follicular lymphoma, mantle cell lymphoma, Monoclonal Gammopathy of Unknown Significance (MGUS), Waldenstrom's Macroglobulinemia (WM), Primary/Systemic Amyloidosis patient tumor cells, and chronic lymphocytic leukemia. Another example of a CD48 expressing cancer that can be treated using the methods disclosed herein is acute myelogenous leukemia.

Definitions

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, for example, U.S. Pat. No. 4,816,567). The "monoclonal antibodies" may also be isolated from phage antibody libraries using the techniques described in Clackson et al. (1991) *Nature,* 352:624-628 and Marks et al. (1991) *J. Mol. Biol.,* 222:581-597, for example or may be made by other methods. The antibodies described herein are monoclonal antibodies.

Antibodies are typically provided in isolated form. This means that an antibody is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies are at least 60%, 70%, 80%, 90%, 95 or 99% w/w pure of interfering proteins and contaminants from production or purification. Antibodies, including isolated antibodies, can be conjugated to cytotoxic agents and provided as antibody drug conjugates.

An "isolated" polynucleotide refers to a polynucleotide that has been identified and separated and/or recovered from components of its natural.

Specific binding of a monoclonal antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. The CD48 directed antibody-drug conjugates and anti-CD48 antibodies specifically bind to CD48.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the subscript and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes). The mature variable regions of each light/heavy chain pair form the antibody binding site. Thus, an intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering system) in which corresponding residues between different heavy chain variable regions or between different light chain variable regions are assigned the same number. Numbering of the heavy chain constant region is via the EU index as set forth in Kabat (Kabat, *Sequences of Proteins of Immunological Interest* (National Institutes of Health, Bethesda, Md., 1987 and 1991).

The term "antibody" includes intact antibodies and antigen binding fragments thereof. An "intact antibody" is one which comprises an antigen-binding variable region as well as a light chain constant domain (C$_L$) and heavy chain constant domains, C$_H$1, C$_H$2, C$_H$3 and C$_H$4, as appropriate for the antibody class. The constant domains may be native sequence constant domains (e.g., human native sequence constant domains) or amino acid sequence variant thereof. Antibody fragments compete with the intact antibody from which they were derived for specific binding to the target including separate heavy chains, light chains Fab, Fab', $F(ab')_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$—$V_H$—$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

The term "therapeutically effective amount" or 'effective amount" refers to an amount of the antibody-drug conjugate that is effective to treat a disease or disorder in a mammal. In the case of cancer, a therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit tumor growth; and/or relieve one or more of the symptoms associated with the cancer. For cancer therapy, efficacy can, for example, be measured by assessing the time to disease progression (TTP) and/or determining the response rate (RR). The term "effective regimen" refers to a combination of amount of the conjugate being administered and dosage frequency adequate to accomplish treatment of the disorder.

The terms "treat" or "treatment," unless otherwise indicated by context, refer to therapeutic treatment wherein the object is to inhibit or slow down (lessen) an undesired physiological change or disorder, such as the development or spread of cancer. Beneficial or desired clinical results include, but are not limited to, alleviation of symptoms, diminishment of extent of disease, a stabilized (i.e., not worsening) state of disease, delay or slowing of disease progression, amelioration or palliation of the disease state, and remission (whether partial or complete), whether detectable or undetectable. "Treatment" can also mean prolonging survival as compared to expected survival if not receiving treatment. Those in need of treatment include those with detectable disease. Those in need of treatment can also include those with undetectable disease, e.g., patients that have achieved a complete response after treatment for the CD48 expressing disorder but are in need of therapy in order to prevent relapse.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD48 antibody or antibody-drug conjugate is administered to a subject.

The phrase "pharmaceutically acceptable salt," refers to pharmaceutically acceptable organic or inorganic salts. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Solvates in the context of the invention are those forms of the compounds of the invention that form a complex in the solid or liquid state through coordination with solvent molecules. Hydrates are one specific form of solvates, in which the coordination takes place with water. Preferred solvates in the context of the present invention are hydrates.

Unless otherwise apparent from the context, the term "about" encompasses values within a standard deviation of a stated value.

BRIEF DESCRIPTION OF THE DRAWINGS

FIG. 1 shows the amino acid sequences for the heavy chain variable region of the murine MEM102 antibody and the humanized vHA, vHB, and vHC heavy chain and selected human germline acceptor variable region sequences.

DETAILED DESCRIPTION

Figure 2:
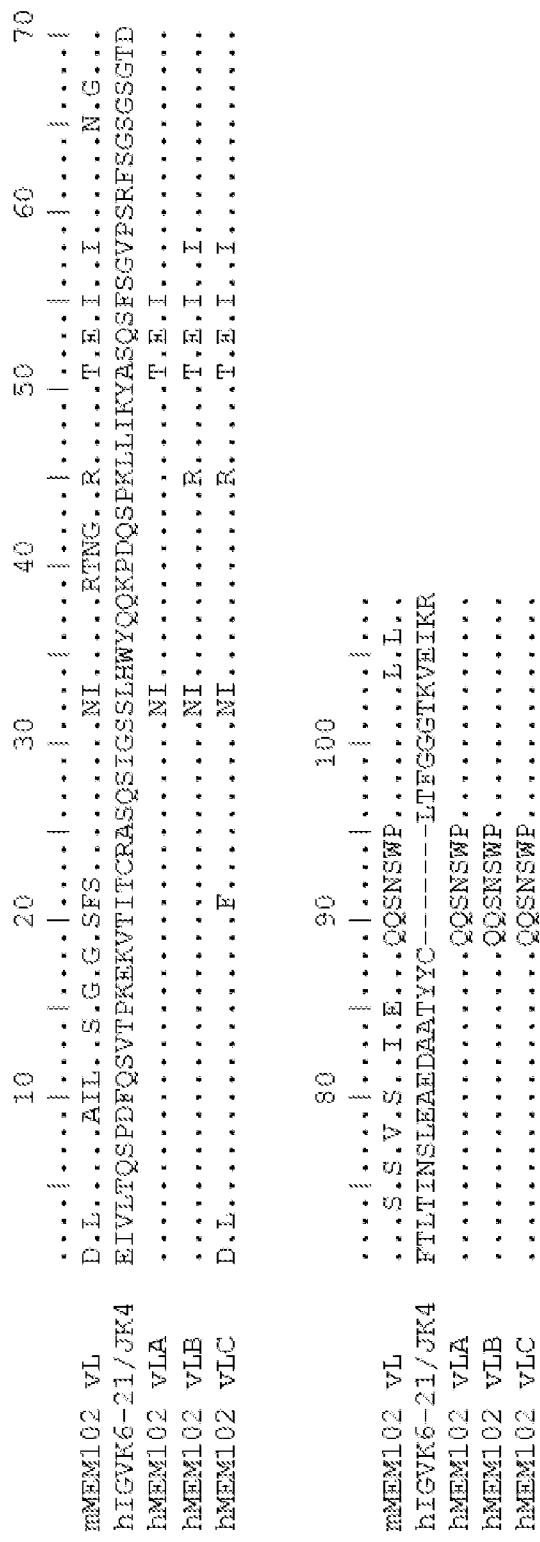
FIG. 2 shows the amino acid sequences for the light chain variable region of the murine MEM102 antibody and the humanized vLA, vLB, and vLC light chain and selected human germline acceptor variable region sequences.

The present invention is based, in part, on the discovery that antibody-drug conjugates, including pegylated-MMAE antibody-drug conjugates targeted to CD48 are particularly effective at killing CD48+ expressing cells. In particular, it was found that a high affinity MEM102 humanized antibody could be constructed using as the heavy chain variable region acceptor sequence the hIgG VH7-4-1/hIgG-JH5 heavy chain variable region human germline. For the light chain variable region, a preferred acceptor sequence is the hIgG-VK6-21/hIgG-JK4 light chain variable region human germline. Notably, the high affinity MEM102 humanized antibody was constructed without the need for performing affinity maturation and while retaining the identity of the CDRs of the murine antibody. The high affinity MEM102 humanized antibody was also effective at drug delivery as part of an antibody drug conjugate. When conjugated to a SGD-5088 pegylated-MMAE drug-linker, the resultant hMEM102-MDpr-PEG(12)-gluc-MMAE 8-load conjugate was highly active against a panel of multiple myeloma cell lines.

Target Molecules

Unless otherwise indicated, CD48 refers to human CD48. An exemplary human sequence is assigned GenBank accession number CAG33293.1.

Antibodies of the Invention

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence.

Thus, a humanized antibody is an antibody having some or all CDRs entirely or substantially from a non-human donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and diabodies, a humanized antibody typically comprises a humanized heavy chain and a humanized light chain. A CDR in a humanized or human antibody is substantially from or substantially identical to a corresponding CDR in a non-human antibody when at least 60%, 85%, 90%, 95% or 100% of corresponding residues (as defined by Kabat) are identical between the respective CDRs. In some embodiments, a CDR in a humanized antibody or human antibody is substantially from or substantially identical to a corresponding CDR in a non-human antibody when there are no more than 3 conservative amino acid substitutions in each CDR. The variable region framework sequences of an antibody chain or the constant region of an antibody chain are substantially from a human variable region framework sequence or human constant region respectively when at least 70%, 80%, 85%, 90%, 95% or 100% of corresponding residues defined by Kabat are identical. In some humanized antibodies of the present invention, there are no backmutations in the heavy chain variable framework region of the antibody and no backmutations in the light chain variable region of the antibody.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

The invention provides antibodies directed against the CD48 antigen. Preferred antibodies are chimeric or humanized antibodies derived from the murine MEM102 antibody. A preferred acceptor sequence for the heavy chain variable region is the hIgG VH7-4-1/hIgG-JH5 heavy chain variable region human germline. For the light chain variable region, a preferred acceptor sequence is the hIgG-VK6-21/hIgG-JK4 light chain variable region human germline.

An exemplary anti-CD48 antibody is a humanized antibody that includes the heavy chain CDRs as set forth in SEQ ID NO:1 and the light chain CDRs as set forth in SEQ ID NO:2 and additionally has a mature heavy chain variable region with at least 90%, 91%, 92%, 93%, 94% or 95% identity to SEQ ID NO:1 and a mature light chain variable region with at least 90%, 91%, 92%, 93%, 94% or 95% identity to SEQ ID NO:2. The CDRs are as defined by Kabat.

Humanized forms of the mouse MEM102 antibody include three exemplified humanized heavy chain mature variable regions (HA-HC) and three exemplified humanized light chain mature variable regions (LA-LC). The permutations of these chains include HALA, HALB, HALC, HBLA, HBLB, HBLC, HCLA, HCLB, and HCLC. Of these permutations, HALA is preferred. HALA comprises the heavy chain set forth in SEQ ID NO:1 and light chain set forth in SEQ ID NO:2. Any one of HALB, HALC, HBLA, HBLB, HBLC, HCLA, HCLB, and HCLC can be used, however, in place of HALA.

In some aspects, the apparent dissociation constant (kd) of the humanized MEM102 antibodies for human CD48 is preferably within a range of 0.1 nM to 10 nM, even more preferably within a range of 0.1 nM to 5 nM, even preferably within a range of 1 nM to 3 nM or 2 nM to about 3 nM. In some aspect, the antibodies of the present invention have an apparent dissociation constant within a range of 0.1 to 2.0 times, or even 0.5 to 4 times that of the apparent dissociation constant of the murine MEM102 antibody for human CD48. In some aspects, the apparent dissociation constant (kd) of the antibodies for human CD48 is about 5.0.

Selection of Constant Region

Heavy chain and light chain variable regions of humanized MEM102 antibodies can be linked to at least a portion of a human constant region. The choice of constant region can depend, in part, whether antibody-dependent cell-mediated cytotoxicity, antibody dependent cellular phagocytosis and/or complement dependent cytotoxicity are desired. For example, human isotypes IgG1 and IgG3 have strong complement-dependent cytotoxicity, human isotype IgG2 has weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain subscript domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

The constant region can be modified to allow for site specific conjugation of a drug-linker. Such techniques include the use of naturally occurring or engineered cysteine residues, disulfide bridges, poly-histidine sequences, glyco-engineering tags, and transglutaminase recognition sequences. An exemplary substitution for site specific conjugation using bacterial transglutaminase is N297S or N297Q. An exemplary substitution for site specific conjugation using an engineered cysteine is S239C. Antibody fragments can also be modified for site-specific conjugation of a drug-linker, see for example, Kim et al., Mol Cancer Ther 2008; 7(8).

Expression of Recombinant Antibodies

Humanized or chimeric MEM102 antibodies can be produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

Nucleic Acids

The invention further provides nucleic acids encoding any of the humanized heavy and light chains described herein. Typically, the nucleic acids also encode a signal peptide fused to the mature heavy and light chain variable regions. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In one embodiment, this disclosure provides an isolated polynucleotide encoding an antibody heavy chain variable region comprising the amino acid sequence as set forth in HA, HB, or HC. For example, the isolated polynucleotide can encode an antibody heavy chain variable region comprising the amino acid sequence of SEQ ID NO:1. This isolated polynucleotide can further encode a human IgG heavy chain constant region. The isotype of the IgG constant region is, e.g., IgG1, IgG2, IgG3, or IgG4. In one embodiment, the isotype of the IgG constant region is IgG1. In another embodiment, the encoded IgG1 constant region has an amino acid sequence comprising a substitution at residue 239, according to the EU index as set forth in Kabat system, i.e., S239C. The disclosure also provides an expression vector comprising the isolated polynucleotide encoding the antibody heavy chain variable region comprising the amino acid sequence as set forth in HA, HB, or HC (e.g., SEQ ID NO:1 or variants thereof), and further, a host cell comprising that expression vector. In some embodiments, the host cell is a mammalian host cell, e.g., a CHO cell.

In another embodiment, this disclosure provides an isolated polynucleotide encoding an antibody light chain variable region comprising the amino acid sequence as set forth in LA, LB or LC. For example, an isolated polynucleotide encoding an antibody light chain variable region comprising the amino acid sequence of SEQ ID NO:2. This isolated polynucleotide can further encode a human IgG light chain constant region. The isotype of the IgG light chain constant region is, e.g., a kappa constant region. The disclosure also provides an expression vector comprising the isolated polynucleotide encoding the antibody light chain variable region comprising the amino acid sequence as set forth in LA or LB or LC (e.g., SEQ ID NO:2 or variants thereof), and further, a host cell comprising that expression vector. In some embodiments, the host cell is a mammalian host cell, e.g., a CHO cell.

In another embodiment, this disclosure provides an isolated polynucleotide or polynucleotides encoding an antibody heavy chain variable region comprising the amino acid sequence of SEQ ID NO:1 and an antibody light chain variable region comprising the amino acid sequence of SEQ ID NO:2, the heavy chain variable domain and the light chain variable domain forming an antibody or antigen binding fragment that specifically binds to human CD48. This disclosure also provides an expression vector comprising the isolated polynucleotide or polynucleotides the encode the antibody heavy chain variable region comprising the amino acid sequence of SEQ ID NO:1 and the antibody light chain variable region comprising the amino acid sequence of SEQ ID NO:2. A host cell comprising the expression vector or vectors is also provided. The host cell is preferably a mammalian cell, e.g., a CHO cell.

In another embodiment, this disclosure provides first and second vectors comprising a polynucleotide encoding an antibody heavy chain variable region comprising the amino acid sequence of SEQ ID NO:1 and a polynucleotide encoding an antibody light chain variable region comprising the amino acid sequence of SEQ ID NO:2, the heavy chain variable domain and the light chain variable domain forming an antibody or antigen binding fragment that specifically binds to human CD48. Host cell comprising the vectors are provided, preferably mammalian host cells, such as a CHO cell.

Antibody-Drug Conjugates

Anti-CD48 antibodies can be conjugated to therapeutic agents, diagnostic agents or stabilizing agents to form antibody conjugates. Anti-CD48 antibodies conjugated to therapeutic agents are referred to herein as antibody-drug conjugates (ADCs). Exemplary therapeutic agents have cytostatic or cytotoxic effect and can also be referred to as cytotoxic agents or cytostatic agents. Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[1,4]benzodiazepines, indolinobenzodiazepines, and oxazolidinobenzodiazepines including pyrrolo[1,4]benzodiazepine dimers, indolinobenzodiazepine dimers, and oxazolidinobenzodiazepine dimers) and vinca alkaloids.

Techniques for conjugating therapeutic agents to proteins, and in particular to antibodies, are well-known. (See, e.g., Alley et al., Current Opinion in Chemical Biology 2010 14:1-9; Senter, Cancer J., 2008, 14(3):154-169.) Typically, the therapeutic agent is conjugated to the antibody via a linker unit. The linker unit can be cleavable or non-cleavable. For example, the therapeutic agent can be attached to the antibody with a cleavable linker that is sensitive to cleavage in the intracellular environment of the CD48-expressing cancer cell but is not substantially sensitive to the extracellular environment, such that the conjugate is cleaved from the antibody when it is internalized by the CD48-expressing cancer cell (e.g., in the endosomal, lysosomal environment, or in the caveolear environment). In another example, the therapeutic agent can be conjugated to the antibody via a non-cleavable linker and drug release is by total antibody degradation following internalization by the CD48-expressing cancer cell.

Typically, the ADC will comprise a linker region between the cytotoxic or cytostatic agent and the anti-CD48 antibody. As noted supra, typically, the linker can be cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, Pharm. Therapeutics 83:67-123, 1999). Most typical are peptidyl linkers that are cleavable by enzymes that are present in CD48-expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide). The linker can also be a carbohydrate linker, including a sugar linker that is cleaved by an intracellular glycosidase (e.g., a glucuronide linker cleavable by a glucuronidase).

The linker also can be a non-cleavable linker, such as an maleimido-alkylene- or maleimide-aryl linker that is directly attached to the therapeutic agent and released by proteolytic degradation of the antibody.

The anti-CD48 antibody can be conjugated to the linker via a heteroatom of the antibody. These heteroatoms can be present on the antibody in its natural state or can be introduced into the antibody. In some aspects, the anti-CD48 antibody will be conjugated to the linker via a nitrogen atom of a lysine residue. In other aspects, the anti-CD48 antibody will be conjugated to the linker via a sulfur atom of a cysteine residue. The cysteine residue can be naturally-occurring or one that is engineered into the antibody. Methods of conjugating linkers and drug-linkers to antibodies via lysine and cysteine residues are known in the art.

Exemplary antibody-drug conjugates include auristatin based antibody-drug conjugates (i.e., the drug component is an auristatin drug). Auristatins bind tubulin, have been shown to interfere with microtubule dynamics and nuclear and cellular division, and have anticancer activity. Typically the auristatin based antibody-drug conjugate comprises a linker between the auristatin drug and the anti-CD48 antibody. The linker can be, for example, a cleavable linker (e.g., a peptidyl linker, a carbohydrate linker) or a non-cleavable linker (e.g., linker released by degradation of the antibody). Auristatins include MMAF, and MMAE. The synthesis and structure of exemplary auristatins are described in U.S. Pat. Nos. 7,659,241, 7,498,298, 2009-0111756, 2009-0018086, and U.S. Pat. No. 7,968,687 each of which is incorporated herein by reference in its entirety and for all purposes.

Other exemplary antibody-drug conjugates include maytansinoid antibody-drug conjugates (i.e., the drug component is a maytansinoid drug), and benzodiazepine antibody drug conjugates (i.e., the drug component is a benzodiazepine (e.g., pyrrolo[1,4]benzodiazepine dimers (PBD dimer), indolinobenzodiazepine dimers, and oxazolidinobenzodiazepine dimers)).

A preferred PBD dimer for use in the present invention is represented by formula I. The preferred stereochemistry of the PBD dimer is as shown in formula Ia:

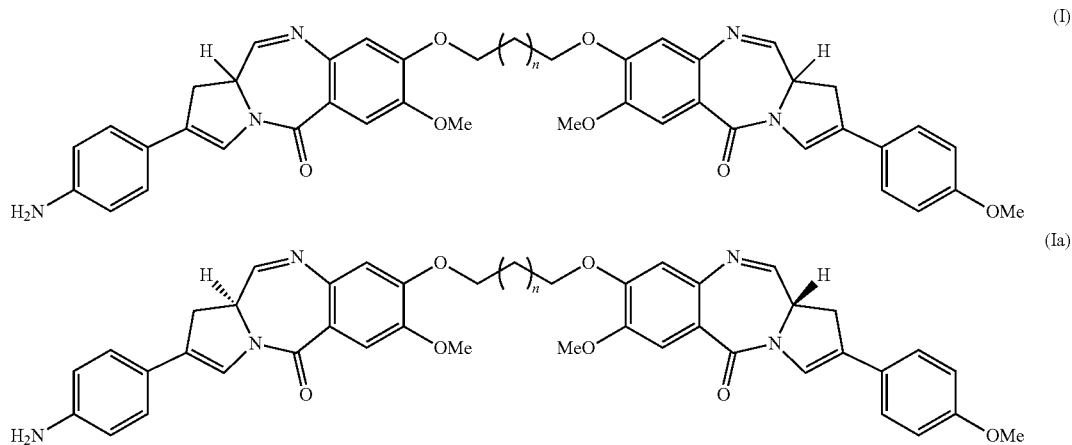

or a pharmaceutically salt, solvate, or solvate of the salt; wherein the subscript n is 1 or 3.

Solvates of formula (I) and (Ia) are typically formed from addition of water or alcoholic solvent across the imine functional group of one or both PBD monomers to form carbinolamine(s) and/or carbinolamine ethers. For example, at the N10-C11 position, there can be an imine (N=C), a carbinolamine (NH—CH(OH)), or a carbinolamine ether (NH—CH(OMe)) as represented by formulas I' and Ia' below:

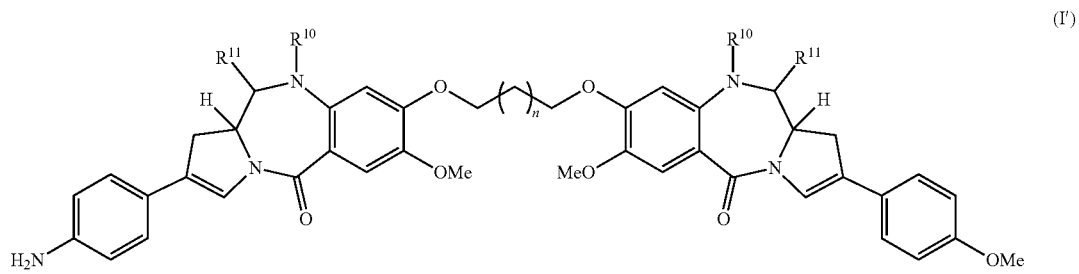

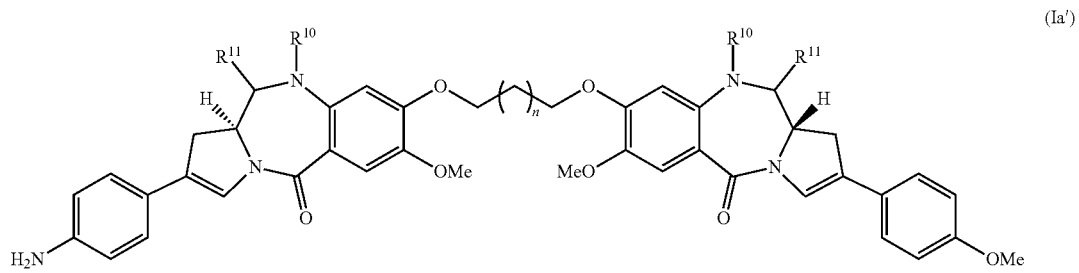

wherein either:

(a) $R^{10}$ is H, and $R^{11}$ is OH or $OR^A$, where $R^A$ is saturated $C_{1-4}$ alkyl (preferably methyl); or (b) $R^{10}$ and $R^{11}$ form a nitrogen-carbon double bond between the nitrogen and carbon atoms to which they are bound; or (c) one of $R^{10}$ is H, and $R^{11}$ is OH or $OR^A$, where $R^A$ is saturated $C_{1-4}$ alkyl (preferably methyl); and the other of $R^{10}$ and $R^{11}$ form a nitrogen-carbon double bond between the nitrogen and carbon atoms to which they are bound.

The PBD dimer of formula I or Ia (or a pharmaceutically salt, solvate, or solvate of the salt thereof) is typically linked to the antibody via a Linker Unit, LU. The Linker Unit acts to release the PBD dimer of formula I or Ia (or a pharmaceutically salt, solvate, or solvate of the salt thereof) at the target site (e.g., inside the cancer cell). A PBD drug-linker compound for use in the present invention is represented below by formula II (preferred stereochemistry as shown in IIa) wherein LU is a Linker Unit. The Linker Unit can be, for example, a cleavable peptide Linker Unit (e.g., a linker comprising the valine-alanine peptide) or a cleavable disulfide Linker Unit:

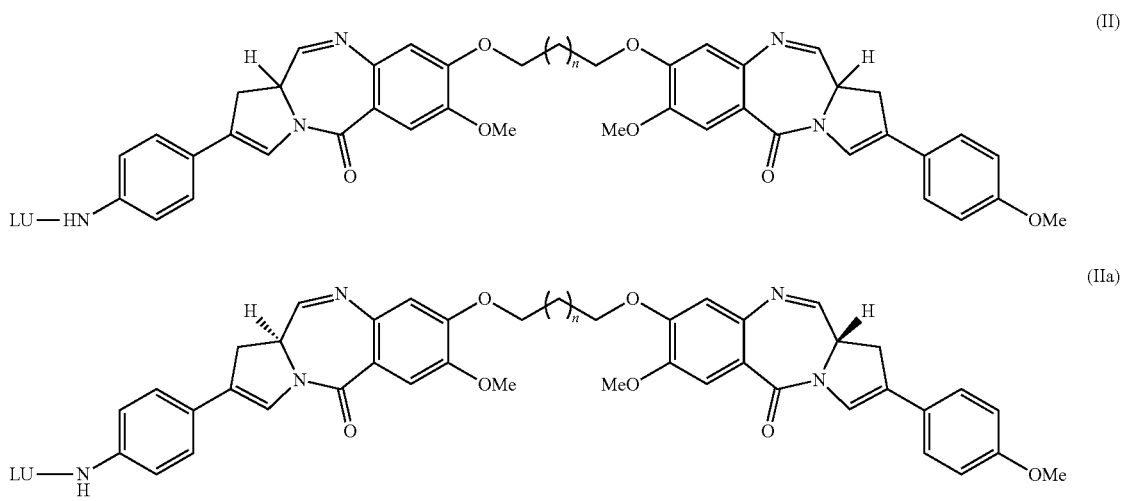

or a pharmaceutically salt, solvate, or solvate of the salt; wherein the subscript n is 1 or 3.

A preferred PBD drug-linker compound for use in the present invention is represented by Formula III below:

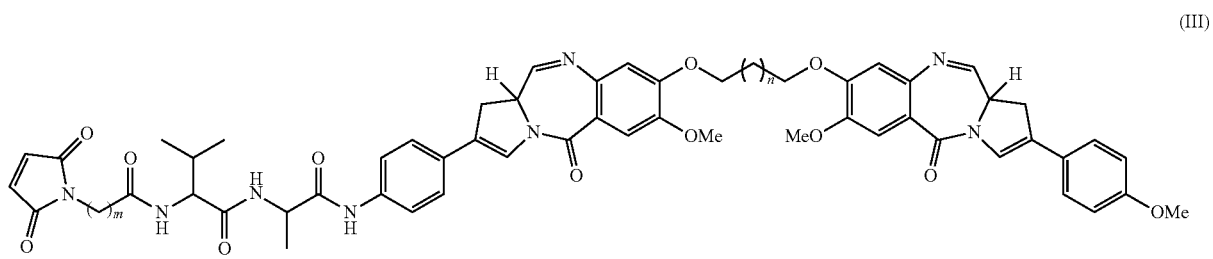

or a pharmaceutically salt, solvate, or solvate of the salt; wherein the subscript n is 1 or 3 and the subscript m is an integer from 2 to 5.

The preferred stereochemistry of the PBD drug component of the drug-linker is as shown in Formula IIIa below:

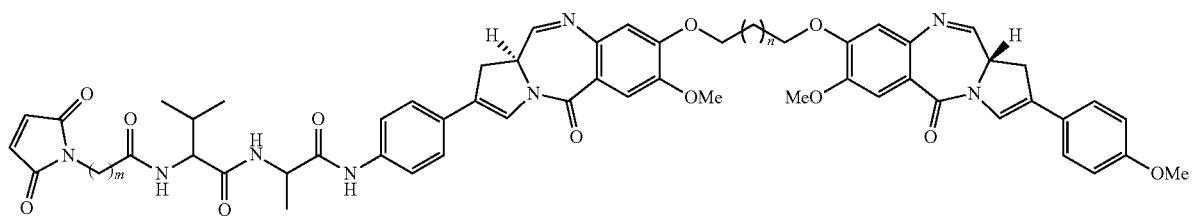
(IIIa)

The preferred stereochemistry of the PBD drug and linker components is as shown in Formula IIIb below:

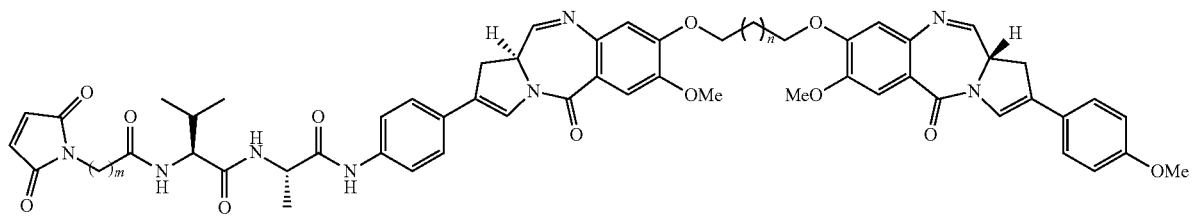
(IIIb)

The PBD drug-linker is conjugated to an anti-CD48 antibody to produce a CD48 targeted antibody-drug conjugate. For example, the antibody can be conjugated to a drug-linker of formula II or formula III. An exemplary CD48 targeted antibody-drug conjugate is shown below in formulas IV, IVa, and IVb:

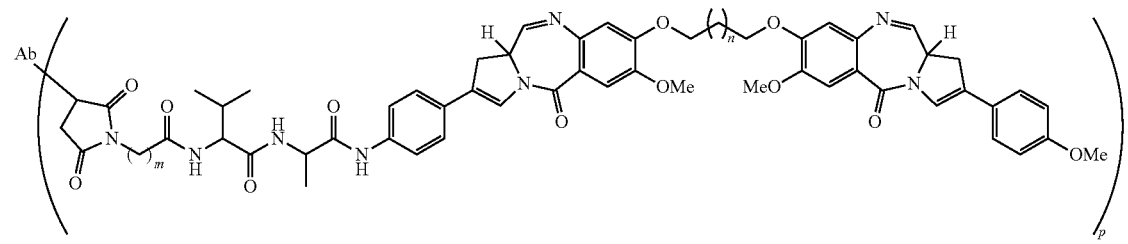
(IV)

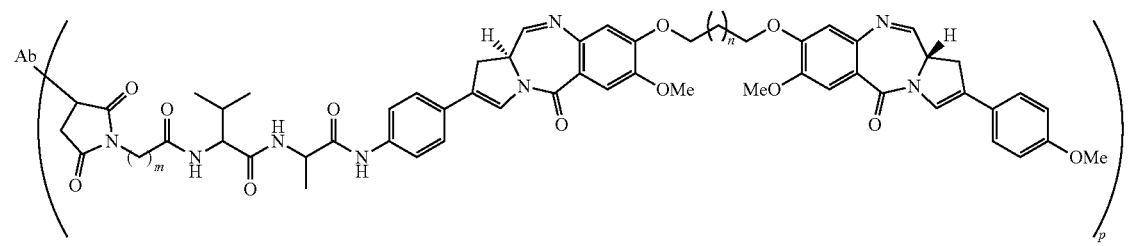
(IVa)

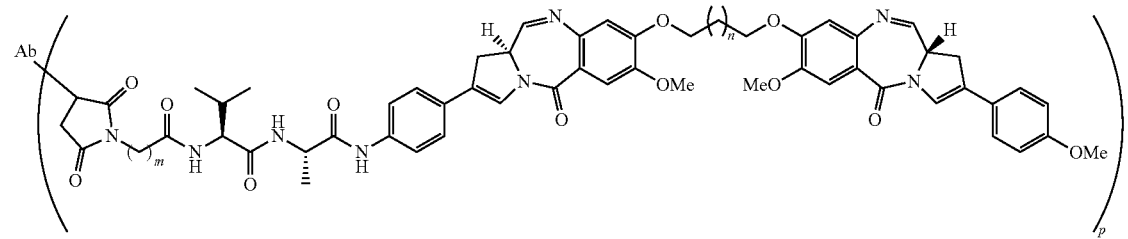
(IVb)

or a pharmaceutically salt, solvate, or solvate of the salt; wherein the subscript n is 1 or 3; the subscript m is an integer from 2 to 5; and the subscript p is from 1 to 4.

Exemplary drug-linkers include MMAE drug-linkers. The present inventors have found that the incorporation of a polyethylene glycol polymer as a side chain into a cleavable β-glucuronide MMAE drug-linker provides antibody drug-conjugates with decreased plasma clearance and increased antitumor activity in xenograft models as compared to a non-PEGylated control. Accordingly, particularly advantageous drug-linkers for attachment to the antibodies of the present invention are as follows:

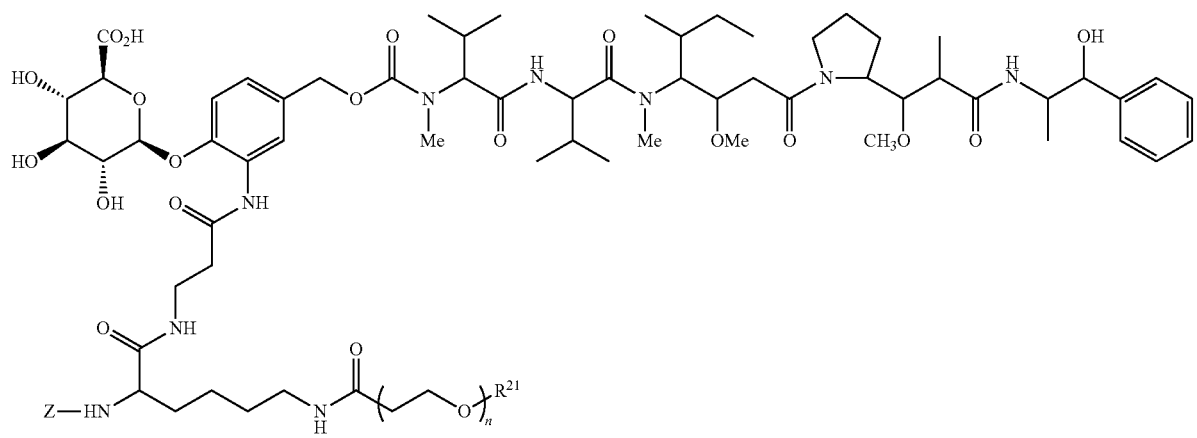

(V)

or a pharmaceutically acceptable salt thereof.

A preferred stereochemistry for such drug-linker is shown below:

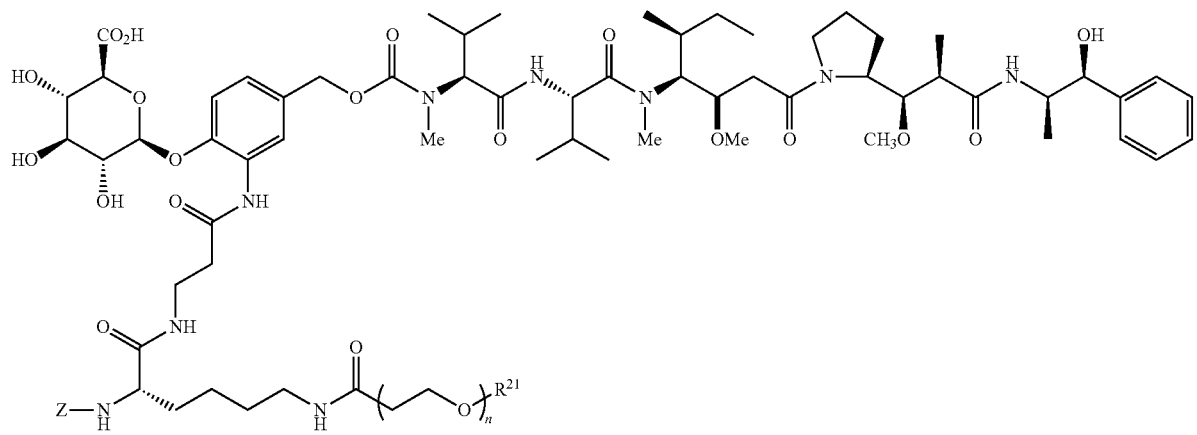

(Va)

or a pharmaceutically acceptable salt thereof wherein for formulas V and Va, Z represents an organic moiety having a reactive site capable of reacting with a functional group on the antibody to form a covalent attachment thereto, n ranges from 8 to 36 and most preferably ranges from 8 to 14 (most preferably 12), $R^{21}$ is a capping unit for the polyethylene glycol moiety, preferably —$CH_3$ or —$CH_2CH_2CO_2H$.

A preferred Z moiety is a maleimido-containing moiety. Particularly preferred Z moieties are shown in the drug-linkers below:

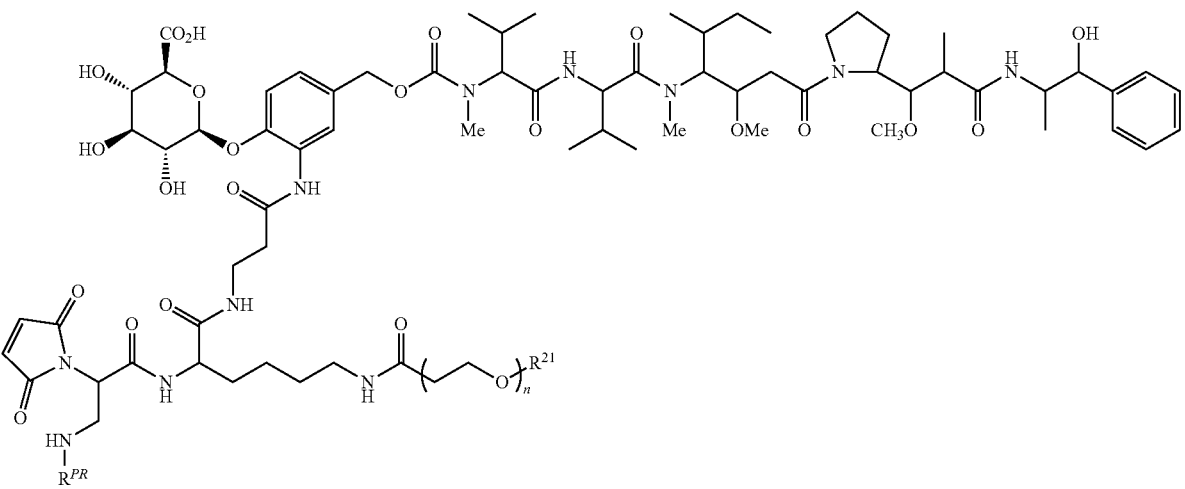
(VI)
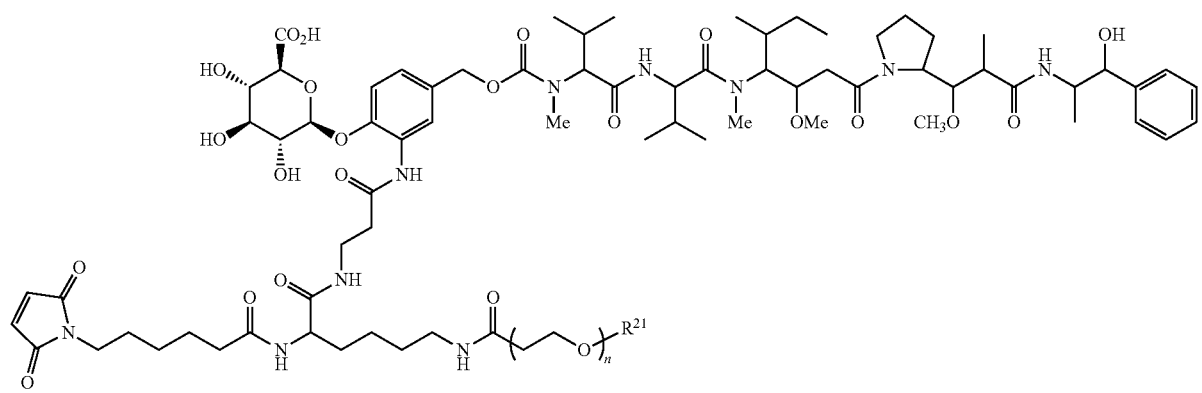
(VII)
or a pharmaceutically acceptable salt thereof.
A preferred stereochemistry for such drug-linkers is shown below:
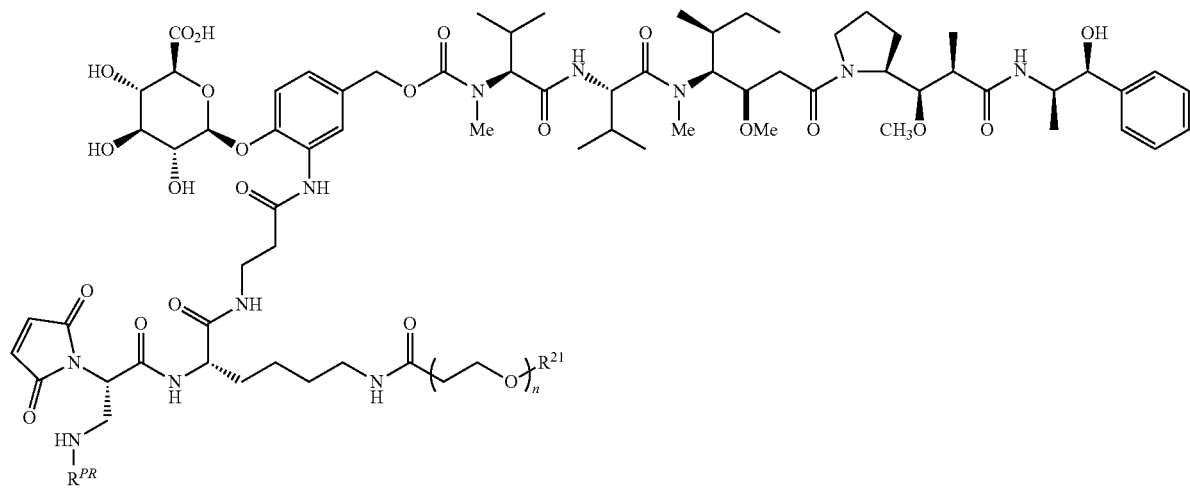
(VIa)

-continued

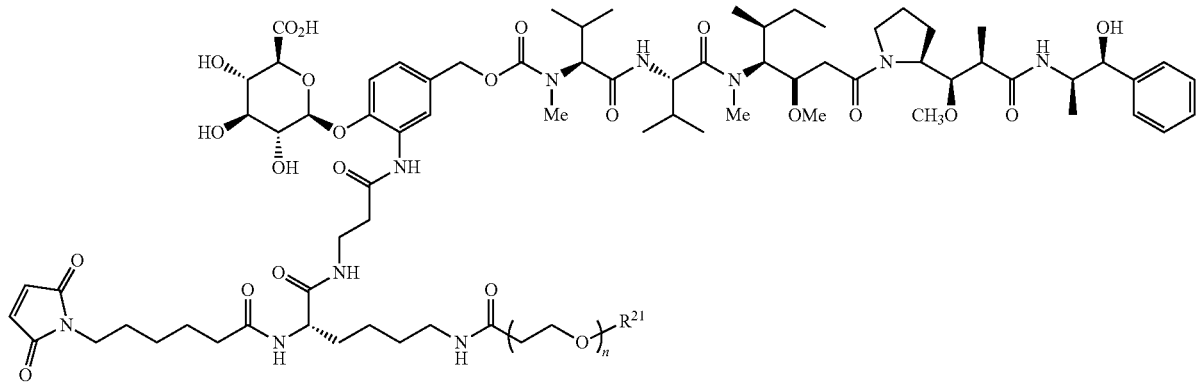

(VIIa)

or a pharmaceutically acceptable salt thereof wherein for formulas VI, VIa, VII and VIIa, n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —CH$_3$ or —CH$_2$CH$_2$CO$_2$H.

As noted above, $R^{PR}$ can be hydrogen or a protecting group. Protective groups as used herein refer to groups which selectively block, either temporarily or permanently, a reactive site in a multifunctional compound. A protecting group is a suitable protecting group when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. Suitable amine protecting groups include acid-labile nitrogen protecting groups, including those provided by Isidro-Llobel et al. "Amino acid-protecting groups" Chem. Rev. (2009) 109: 2455-2504. Typically, an acid-labile nitrogen-protecting group transforms a primary or secondary amino group to its corresponding carbamate and includes t-butyl, allyl, and benzyl carbamates.

As noted above, $R^{21}$ is a capping unit for the polyethylene glycol moiety. As will be appreciated by the skilled artisan, polyethylene glycol units can be terminally capped with a wide diversity of organic moieties, typically those that are relatively non-reactive. Alkyl and substituted alkyl groups are preferred, including, for example, —C$_{1-10}$ alkyl, —C$_{2-10}$ alkyl-CO$_2$H, —C$_{2-10}$ alkyl-OH, —C$_{2-10}$ alkyl-NH$_2$, C$_{2-10}$ alkyl-NH(C$_{1-3}$ alkyl), or C$_{2-10}$ alkyl-N(C$_{1-3}$ alkyl)$_2$.

Generally, there are 1 to 16 drug-linkers attached to each antibody.

Drug Loading—"p"

Referring to the CD48 targeted antibody-drug conjugates, the subscript p represents the drug load and, depending on the context, can represent the number of molecules of drug-linker molecules attached to an individual antibody molecule and as such, is an integer value, or can represent an average drug load and, as such, can be an integer or non-integer value but is typically a non-integer value. An average drug load represents the average number of drug-linker molecules per antibody in a population. Often, but not always, when we refer to an antibody, e.g., a monoclonal antibody, we are referring to a population of antibody molecules. In a composition comprising a population of antibody-drug conjugate molecules, the average drug load is an important quality attribute as it determines the amount of drug that can be delivered to a target cell. The percentage of unconjugated antibody molecules in the composition is included in the average drug load value.

In preferred aspects of the present invention, the average drug load when referring to a composition comprising a population of antibody-drug conjugate compounds is from 1 to about 16, preferably about 2 to about 14, more preferably about 2 to about 10. For PBD antibody drug conjugates, such as those exemplified herein, a particularly preferred average drug load is about 2. In some aspects, the actual drug load for individual antibody molecules in the population of antibody-drug conjugate compounds is from 1 to 4, 1 to 3 or 1 to 2 with a predominant drug loading of 2. In preferred aspects, the average drug load of 2 is achieved via site specific conjugation techniques (e.g., engineered cysteines introduced to the antibody including at position 239, according to the EU Index numbering system).

For the MMAE PEGylated ADCs, such as those exemplified herein, a particularly preferred average drug load is about 8. In exemplary embodiments, the drug-linkers are conjugated to the cysteine residues of the reduced interchain disulfides. In some aspects, the actual drug load for individual antibody molecules in the population of antibody-drug conjugate compounds is from 1 to 10 (or from 6 to 10 or from 6 to 8) with a predominant drug loading of 8. A higher drug load can be achieved, for example, if, in addition to the interchain disulfides, drug-linker is conjugated to introduced cysteine residues (such as a cysteine residue introduced at position 239, according to the EU index).

Exemplary ADCs include the following:
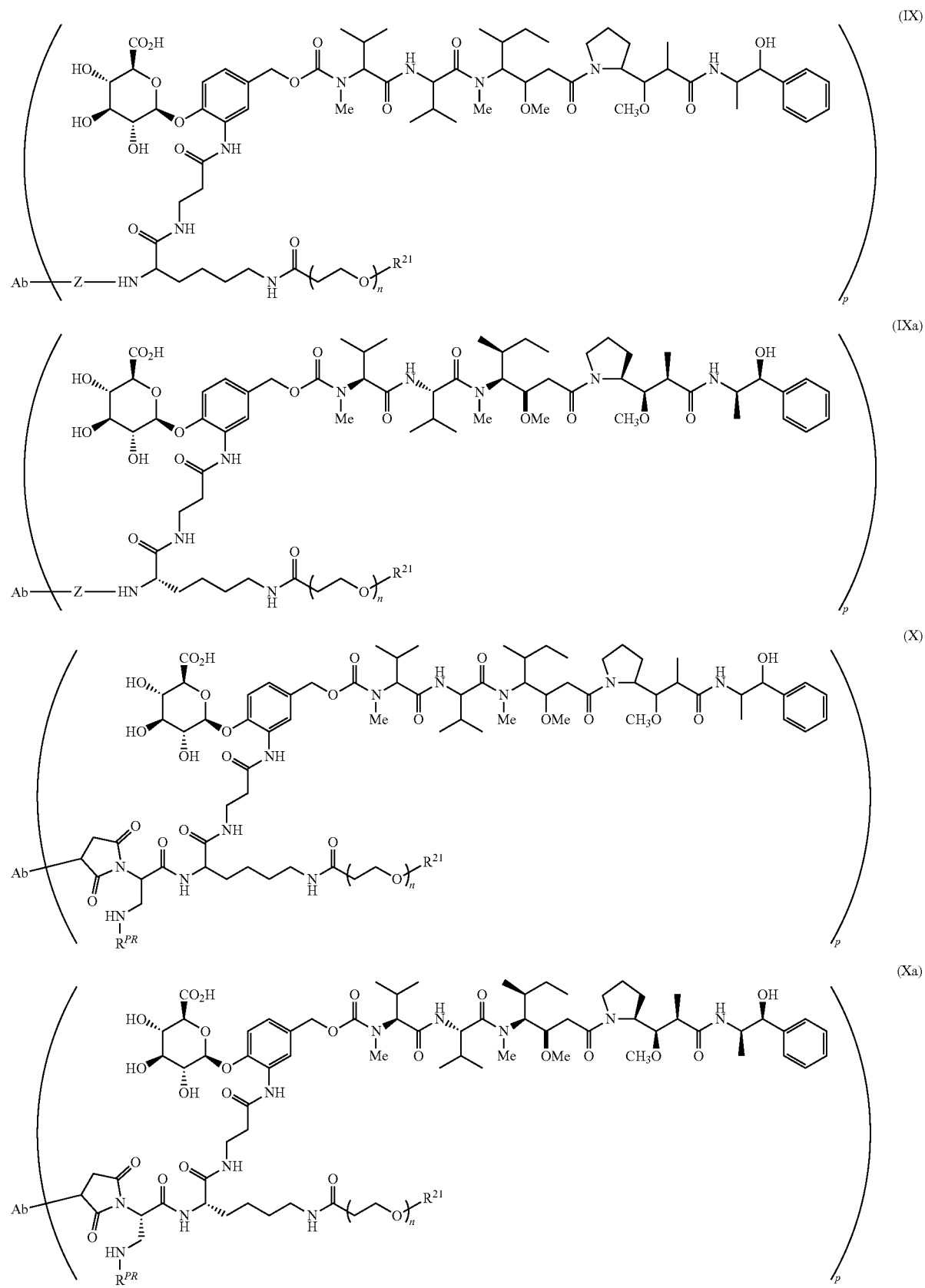

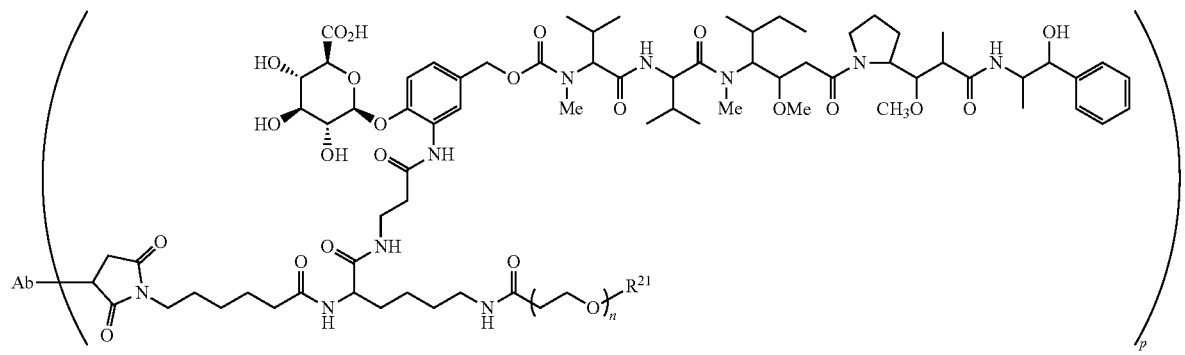

(XI)

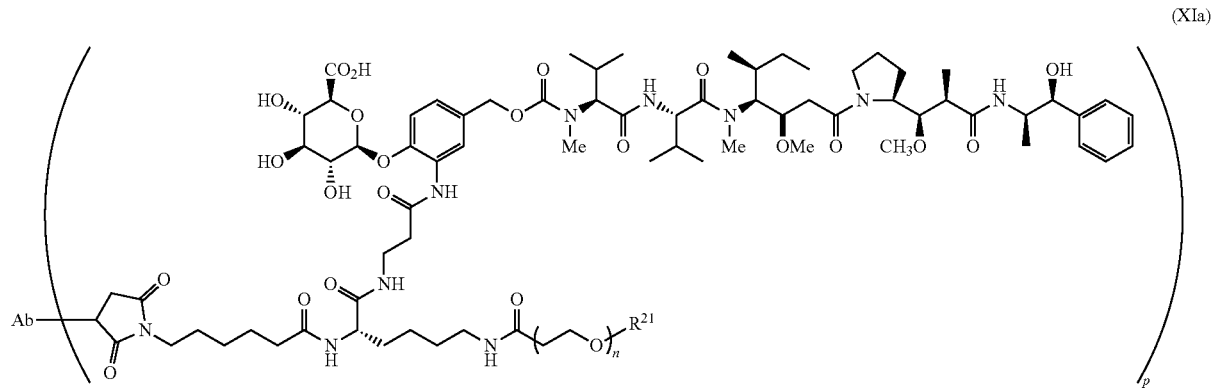

(XIa)

or a pharmaceutically acceptable salt thereof wherein n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —$CH_3$ or —$CH_2CH_2CO_2H$, Ab represents an anti-CD48 antibody and p represents an integer ranging from 1 to 16, preferably 1 to 14, 6 to 12, 6 to 10, or 8 to 10 when referring to individual antibody molecules or to an average drug load of from about 4 or about 6 to about 14, preferably about 8 when referring to a population of antibody molecules.

As noted above, the PEG (polyethylene glycol) portion of the drug linker can range from 8 to 36, however, it has been found that a PEG of 12 ethylene oxide units is particularly preferably. It has been found that longer PEG chains can result in slower clearance whereas shorter PEG chains can result in diminished activity. Accordingly, the subscript n in all of the embodiments above is preferably 8 to 14, 8 to 12, 10 to 12 or 10 to 14 and is most preferably 12.

Polydisperse PEGS, monodisperse PEGS and discrete PEGs can be used to make the PEGylated antibody drug conjugates of the present invention. Polydisperse PEGs are a heteregenous mixture of sizes and molecular weights whereas monodisperse PEGs are typically purified from heterogenous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length. As with the subscript "p", when referring to populations of antibody-drug conjugates, the value for the subscript "n" can be an average number and can be an integer or non-integer number.

In preferred embodiments, covalent attachment of the antibody to the drug-linker is accomplished through a sulfhydryl functional group of the antibody interacting with a maleimide functional group of a drug linker to form a thio-substituted succinimide. The sulfhydryl functional group can be present on the Ligand Unit in the Ligand's natural state, for example, in a naturally-occurring residue (inter-chain disulfide resides), or can be introduced into the Ligand via chemical modification or by biological engineering, or a combination of the two. It will be understood that an antibody-substituted succinimide may exist in hydrolyzed form(s). For example, in preferred embodiments, an ADC is comprised of a succinimide moiety that when bonded to the antibody is represented by the structure of

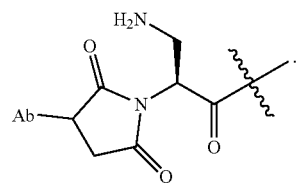

or is comprised of its corresponding acid-amide moiety that when bonded to the antibody is represented by the structure of:

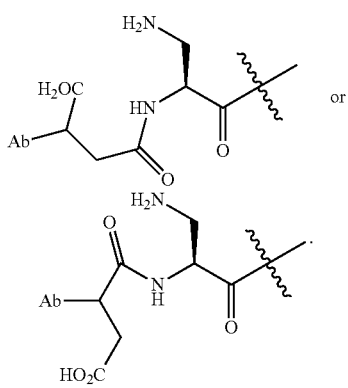

The wavy line indicates linkage to the remainder of the drug-linker.

Therapeutic Applications

The CD48 targeted antibody-drug conjugates described herein can be used to treat a CD48 expressing disorder, such as CD48 expressing cancer. Typically such cancers show detectable levels of CD48 measured at the protein (e.g., by immunoassay) or RNA level. Some such cancers show elevated levels of CD48 relative to noncancerous tissue of the same type, preferably from the same patient. Optionally, a level of CD48 in a cancer is measured before performing treatment.

Examples of cancers associated with CD48 expression include multiple myeloma, and other B cell malignancies, including Hodgkin's disease, non-Hodgkin's lymphoma, Follicular lymphoma, chronic lymphocytic leukemia (CLL), mantle cell lymphoma, Waldenström's Macroglobulinemia, Primary/Systemic Amyloidosis patient tumor cells, MGUS, and Amyloidosis. Some acute myeloid leukemia (AML) cell lines (e.g., AML patient leukemic blast cells) have been observed to express CD48 and thus, patients with AML cancers that express CD48 can be treated using the disclosed CD48 ADCs.

Methods of the present invention include treating a patient that has a cancer that expresses CD48 comprising administering to the patient an antibody-drug conjugate of the present invention. The cancer can be any CD48 expressing cancer, including, for example, multiple myeloma.

CD48 directed antibody-drug conjugates are administered in an effective regimen meaning a dosage, route of administration and frequency of administration that delays the onset, reduces the severity, inhibits further deterioration, and/or ameliorates at least one sign or symptom of cancer.

Exemplary dosages for CD48 directed pegylated-MMAE conjugates are generally from about 1.0 µg/kg to 10.0 mg/kg, or from about 0.1 mg/kg to 5.0 mg/kg or from about 0.5 mg/kg to 1.0, 2.0, or 4.0 µg/kg, although alternate dosages are contemplated. A preferred dose range is from about 0.3 mg/kg to about 2.0 mg/kg.

Administration can be by a variety of administration routes. In certain embodiments, the conjugates are administered parenterally, such as intravenously, intramuscularly, or subcutaneously. For administration of an ADC for the treatment of cancer, the delivery can be into the systemic circulation by intravenous or subcutaneous administration. In a particular embodiment, administration is via intravenous delivery. Intravenous administration can be, for example, by infusion over a period such as 30-90 minutes or by a single bolus injection. In some aspects, administration will be via slow IV push (i.e., over 30-60 seconds) in a peripherally inserted central catheter.

The frequency of administration depends upon many different factors, including means of administration, target site, physiological state of the patient, whether the patient is human or an animal, and other medications administered. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are every three weeks or between once weekly or once monthly over a continuous course of treatment, although more or less frequent dosing is also possible. Another exemplary frequency is administration every six weeks. For subcutaneous administration, an exemplary dosing frequency is daily to monthly, although more or less frequent dosing is also possible.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, conjugates can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of conjugate in a liquid formulation can vary widely. In some aspects, the ADC is present at a concentration from about 0.5 mg/ml to about 30 mg/ml, from about 0.5 mg/ml to about 10 mg/ml, from about 1 mg/ml to about 10 mg/ml, from about 2 mg/ml to about 10 mg/ml, or from about 2 mg/ml to about 5 mg/ml.

Treatment with conjugates of the invention can be combined with chemotherapy, radiation, stem cell treatment, surgery, and other treatments effective against the disorder being treated, including standard of care for the particular disorder being treated. Accordingly, the present invention encompasses methods of treating the disease and disorders described herein as a monotherapy or in combination therapy with, for example, standard of care or investigational drugs for treatment of such diseases and/or disorders. Methods for the treatment of cancer include administering to a patient in need thereof an effective amount of a CD48 directed antibody-drug conjugate of the present invention in combination with an additional anti-cancer agent or other agent to treat cancer.

An exemplary agent for combination therapy is carfilzomib (e.g. KYPROLIS®), a proteasome inhibitor used to treat multiple myeloma (see Siegel D S et al. A phase 2 study of single-agent carfilzomib (PX-171-003-A1) in patients with relapsed and refractory multiple myeloma. *Blood* 2012; 120:2817-2825). Carfilzomib can be administered as an intravenous/IV infusion. In an embodiment, carfilzomib is administered in a combination therapy with a CD48 directed antibody-drug conjugate of the present invention. In a further embodiment, carfilzomib is administered in a combination therapy with an hMEM102 antibody-drug conjugate of the present invention. In a further embodiment, carfilzomib is administered in a combination therapy with an hMEM102-MDpr-PEG(12)-gluc-MMAE 8-load of the present invention.

Carfilzomib can also be administered in a combination therapy with a CD48 directed antibody-drug conjugate of the present invention and an additional agent. Carfilzomib has been combined with various additional agents to treat multiple myeloma. For example, carfilzomib has been combined with lenalidomide and dexamethasone (see Stewart K A et al. Carfilzomib, lenalidomide, and dexamethasone for relapsed multiple myeloma. *N Engl J Med.* 2015; 372:142-152). In an embodiment, carfilzomib is administered in a combination therapy with lenalidomide, dexamethasone, and a CD48 directed antibody-drug conjugate of the present invention. In a further embodiment, carfilzomib is administered in a combination therapy with lenalidomide, dexamethasone, and an hMEM102 antibody-drug conjugate of the present invention. In a further embodiment, carfilzomib is administered in a combination therapy with lenalidomide, dexamethasone, and an hMEM102-MDpr-PEG(12)-gluc-MMAE 8-load of the present invention.

Carfilzomib has also been combined with dexamethasone (see Dimopoulos M D et al. Carfilzomib and dexamethasone versus bortezomib and dexamethasone for patients with relapsed or refractory multiple myeloma (ENDEAVOR): a randomised, phase 3, open-label, multicentre study. *Lancet Oncology* 2016; 17:27-38). In an embodiment, carfilzomib is administered in a combination therapy with dexamethasone and a CD48 directed antibody-drug conjugate of the present invention. In a further embodiment, carfilzomib is administered in a combination therapy with dexamethasone and an hMEM102 antibody-drug conjugate of the present invention. In a further embodiment, carfilzomib is administered in a combination therapy with dexamethasone and an hMEM102-MDpr-PEG(12)-gluc-MMAE 8-load of the present invention.

Carfilzomib has also been combined with panobinostat (see Berdeja J G et al. Phase I/II study of the combination of panobinostat and carfilzomib in patients with relapsed/refractory multiple myeloma. *Haematologica* 2015; 100: 670-676). In an embodiment, carfilzomib is administered in a combination therapy with panobinostat and a CD48 directed antibody-drug conjugate of the present invention. In a further embodiment, carfilzomib is administered in a combination therapy with panobinostat and an hMEM102 antibody-drug conjugate of the present invention. In a further embodiment, carfilzomib is administered in a combination therapy with panobinostat and an hMEM102-MDpr-PEG(12)-gluc-MMAE 8-load of the present invention. Carfilzomib has also been combined with pomalidomide and dexamethasone (see Shah J et al. Carfilzomib, pomalidomide, and dexamethasone (CPD) in patients with relapsed and/or refractory multiple myeloma. Blood 2015; 126: 2284-2290). In an embodiment, carfilzomib is administered in a combination therapy with pomalidomide, dexamethasone, and a CD48 directed antibody-drug conjugate of the present invention. In a further embodiment, carfilzomib is administered in a combination therapy with pomalidomide, dexamethasone, and an hMEM102 antibody-drug conjugate of the present invention. In a further embodiment, carfilzomib is administered in a combination therapy with pomalidomide, dexamethasone, and an hMEM102-MDpr-PEG(12)-gluc-MMAE 8-load of the present invention.

Another exemplary agent for combination therapy is daratumumab (e.g. DARZALEX™) a human monoclonal antibody that binds CD38 (a glycoprotein highly expressed on multiple myeloma cells). Daratumumab can be administered to patients by intravenous infusion to treat multiple myeloma (see Lokhorst H M et al. Targeting CD38 with daratumumab monotherapy in multiple myeloma. *N Engl J Med* 2015; 373:1207-1219). In an embodiment, daratumumab is administered in a combination therapy with a CD48 directed antibody-drug conjugate of the present invention. In a further embodiment, daratumumab is administered in a combination therapy with an hMEM102 antibody-drug conjugate of the present invention. In a further embodiment, daratumumab is administered in a combination therapy with an hMEM102-MDpr-PEG(12)-gluc-MMAE 8-load of the present invention.

Daratumumab can also be administered in a combination therapy with a CD48 directed antibody-drug conjugate of the present invention and an additional agent. Daratumumab has been combined with various additional agents to treat multiple myeloma. For example, daratumumab has been combined with bortezomib and lenalidomide (see Phipps C et al. Daratumumab and its potential in the treatment of multiple myeloma: overview of the preclinical and clinical development. *Ther Adv Hematol* 2015; 6:120-127). In an embodiment, daratumumab is administered in a combination therapy with bortezomib, lenalidomide, and a CD48 directed antibody-drug conjugate of the present invention. In a further embodiment, daratumumab is administered in a combination therapy with bortezomib, lenalidomide, and an hMEM102 antibody-drug conjugate of the present invention. In a further embodiment, daratumumab is administered in a combination therapy with bortezomib, lenalidomide, and an hMEM102-MDpr-PEG(12)-gluc-MMAE 8-load of the present invention.

Daratumumab has also been combined with bortezomib and dexamethasone (see Phipps C et al.). In an embodiment, daratumumab is administered in a combination therapy with bortezomib, dexamethasone, and a CD48 directed antibody-drug conjugate of the present invention. In a further embodiment, daratumumab is administered in a combination therapy with bortezomib, dexamethasone, and an hMEM102 antibody-drug conjugate of the present invention. In a further embodiment, daratumumab is administered in a combination therapy with bortezomib, dexamethasone, and an hMEM102-MDpr-PEG(12)-gluc-MMAE 8-load of the present invention.

Another exemplary agent for combination therapy is elotuzumab (e.g. EMPLICITI™), a monoclonal antibody that binds CD319, or signaling lymphocytic activation molecule F7 (SLAMF7), a marker for malignant multiple myeloma cells. Elotuzumab can be administered to patients by intravenous infusion to treat multiple myeloma (see Zonder J A et al. A phase 1, multicenter, open-label, dose escalation study of elotuzumab in patients with advanced multiple myeloma. *Blood* 2012; 120: 552-559).). In an embodiment, elotuzumab is administered in a combination therapy with a CD48 directed antibody-drug conjugate of the present invention. In a further embodiment, elotuzumab is administered in a combination therapy with an hMEM102 antibody-drug conjugate of the present invention. In a further embodiment, elotuzumab is administered in a combination therapy with an hMEM102-MDpr-PEG(12)-gluc-MMAE 8-load of the present invention.

Elotuzumab can also be administered in a combination therapy with a CD48 directed antibody-drug conjugate of the present invention and an additional agent. Elotuzumab has been combined with various additional agents to treat multiple myeloma. For example, elotuzumab has been combined with lenalidomide and dexamethasone (see Lonial S et al. Elotuzumab therapy for relapsed or refractory multiple myeloma. *N Engl J Med* 2015; 373:621-631;). In an embodiment, elotuzumab is administered in a combination therapy with lenalidomide, dexamethasone, and a CD48 directed antibody-drug conjugate of the present invention. In a further embodiment, elotuzumab is administered in a combination therapy with lenalidomide, dexamethasone, and an hMEM102 antibody-drug conjugate of the present invention. In a further embodiment, elotuzumab is administered in a combination therapy with lenalidomide, dexamethasone, and an hMEM102-MDpr-PEG(12)-gluc-MMAE 8-load of the present invention.

Another exemplary agent for combination therapy is lenalidomide (e.g. REVLIMID®), an immunomodulatory agent given to patients to treat multiple myeloma (see Richardson P G, A randomized phase 2 study of lenalidomide therapy for patients with relapsed or relapsed and refractory multiple myeloma. *Blood* 2006, 108: 3458-3464). Lenalidomide can be packaged as a capsule, pill, or tablet for oral administration. In an embodiment, lenalidomide is administered in a combination therapy with a CD48 directed antibody-drug conjugate of the present invention. In a further embodiment, lenalidomide is administered in a combination therapy with an hMEM102 antibody-drug conjugate of the present invention. In a further embodiment, lenalidomide is administered in a combination therapy with an hMEM102-MDpr-PEG(12)-gluc-MMAE 8-load of the present invention.

Lenalidomide can also be administered in a combination therapy with a CD48 directed antibody-drug conjugate of the present invention and an additional agent. Lenalidomide has been combined with various additional agents that treat multiple myeloma. For example, lenalidomide has been combined with bortezomib and dexamethasone (see Richardson P G et al. Lenalidomide, bortezomib, and dexamethasone combination therapy in patients with newly diagnosed multiple myeloma. *Blood* 2010; 116:679-686). In an embodiment, lenalidomide is administered in a combination therapy with bortezomib, dexamethasone, and a CD48 directed antibody-drug conjugate of the present invention. In a further embodiment, lenalidomide is administered in a combination therapy with bortezomib, dexamethasone, and an hMEM102 antibody-drug conjugate of the present invention. In a further embodiment, lenalidomide is administered in a combination therapy with bortezomib, dexamethasone, and an hMEM102-MDpr-PEG(12)-gluc-MMAE 8-load of the present invention.

Lenalidomide has also been combined with carfilzomib and dexamethasone (see Stewart K A et al.). In an embodiment, lenalidomide is administered in a combination therapy with carfilzomib, dexamethasone, and a CD48 directed antibody-drug conjugate of the present invention. In a further embodiment, lenalidomide is administered in a combination therapy with carfilzomib, dexamethasone, and an hMEM102 antibody-drug conjugate of the present invention. In a further embodiment, lenalidomide is administered in a combination therapy with carfilzomib, dexamethasone, and an hMEM102-MDpr-PEG(12)-gluc-MMAE 8-load of the present invention.

Lenalidomide has also been combined with daratumumab and bortezomib (see Phipps C et al.). In an embodiment, lenalidomide is administered in a combination therapy with daratumumab, bortezomib, and a CD48 directed antibody-drug conjugate of the present invention. In a further embodiment, lenalidomide is administered in a combination therapy with daratumumab, bortezomib, and an hMEM102 antibody-drug conjugate of the present invention. In a further embodiment, lenalidomide is administered in a combination therapy with daratumumab, bortezomib, and an hMEM102-MDpr-PEG(12)-gluc-MMAE 8-load of the present invention.

Lenalidomide has also been combined with elotuzumab and dexamethasone (see Lonial S et al. Elotuzumab therapy for relapsed or refractory multiple myeloma. *N Engl J Med* 2015; 373:621-631). In an embodiment, lenalidomide is administered in a combination therapy with elotuzumab, dexamethasone, and a CD48 directed antibody-drug conjugate of the present invention. In a further embodiment, lenalidomide is administered in a combination therapy with elotuzumab, dexamethasone, and an hMEM102 antibody-drug conjugate of the present invention. In a further embodiment, lenalidomide is administered in a combination therapy with elotuzumab, dexamethasone, and an hMEM102-MDpr-PEG(12)-gluc-MMAE 8-load of the present invention.

Another exemplary agent for combination therapy is bortezomib (e.g. VELCADE®), a proteasome inhibitor given to patients to treat multiple myeloma and mantle cell lymphoma (see Richardson P G et al. A phase 2 study of bortezomib in relapsed, refractory myeloma. *N Engl J Med* 2003; 348:2609-2617). Bortezomib can be administered to patients via intravenous injection. In an embodiment, bortezomib is administered in a combination therapy with a CD48 directed antibody-drug conjugate of the present invention. In a further embodiment, bortezomib is administered in a combination therapy with an hMEM102 antibody-drug conjugate of the present invention. In a further embodiment, bortezomib is administered in a combination therapy with an hMEM102-MDpr-PEG(12)-gluc-MMAE 8-load of the present invention.

Bortezomib can also be administered in a combination therapy with a CD48 directed antibody-drug conjugate of the present invention and an additional agent. Bortezomib has been combined with various additional agents to treat multiple myeloma. For example, bortezomib has been combined with thalidomide and dexamethasone (see Kapoor P et al. Bortezomib combination therapy in multiple myeloma. *Semin Hematol* 2012; 3:228-242). In an embodiment, bortezomib is administered in a combination therapy with thalidomide, dexamethasone, and a CD48 directed antibody-drug conjugate of the present invention. In a further embodiment, bortezomib is administered in a combination therapy with thalidomide, dexamethasone, and an hMEM102 antibody-drug conjugate of the present invention. In a further embodiment, bortezomib is administered in a combination therapy with thalidomide, dexamethasone, and an hMEM102-MDpr-PEG(12)-gluc-MMAE 8-load of the present invention.

Bortezomib has also been combined with dexamethasone, thalidomide, cisplatin, doxorubicin, cyclophosphamide, and etoposide (see Kapoor P et al.). In an embodiment, bortezomib is administered in a combination therapy with dexamethasone, thalidomide, cisplatin, doxorubicin, cyclophosphamide, etoposide, and a CD48 directed antibody-drug conjugate of the present invention. In a further embodiment, bortezomib is administered in a combination therapy with dexamethasone, thalidomide, cisplatin, doxorubicin, cyclophosphamide, etoposide, and an hMEM102 antibody-drug conjugate of the present invention. In a further embodiment, bortezomib is administered in a combination therapy with dexamethasone, thalidomide, cisplatin, doxorubicin, cyclophosphamide, etoposide, and an hMEM102-MDpr-PEG(12)-gluc-MMAE 8-load of the present invention.

Bortezomib has also been combined with daratumumab and lenalidomide (see Phipps C et al.). In an embodiment, bortezomib is administered in a combination therapy with daratumumab, lenalidomide, and a CD48 directed antibody-drug conjugate of the present invention. In a further embodiment, bortezomib is administered in a combination therapy with daratumumab, lenalidomide, and an hMEM102 antibody-drug conjugate of the present invention. In a further embodiment, bortezomib is administered in a combination therapy with daratumumab, lenalidomide, and an hMEM102-MDpr-PEG(12)-gluc-MMAE 8-load of the present invention.

Bortezomib has also been combined with lenalidomide and dexamethasone (see Richardson P G et al. 2010). In an embodiment, bortezomib is administered in a combination therapy with lenalidomide, dexamethasone, and a CD48 directed antibody-drug conjugate of the present invention. In a further embodiment, bortezomib is administered in a combination therapy with lenalidomide, dexamethasone, and an hMEM102 antibody-drug conjugate of the present invention. In a further embodiment, bortezomib is administered in a combination therapy with lenalidomide, dexamethasone, and an hMEM102-MDpr-PEG(12)-gluc-MMAE 8-load of the present invention.

Bortezomib has also been combined with panobinostat and dexamethasone (see Richardson P et al. PANORAMA 2: panobinostat in combination with bortezomib and dexamethasone in patients with relapsed and bortezomib-refractory myeloma. Blood 2013; 122:2331-2337). In an embodiment, bortezomib is administered in a combination therapy with panobinostat, dexamethasone, and a CD48 directed antibody-drug conjugate of the present invention. In a further embodiment, bortezomib is administered in a combination therapy with panobinostat, dexamethasone, and an hMEM102 antibody-drug conjugate of the present invention. In a further embodiment, bortezomib is administered in a combination therapy with panobinostat, dexamethasone, and an hMEM102-MDpr-PEG(12)-gluc-MMAE 8-load of the present invention.

Another exemplary agent for combination therapy is dexamethasone (e.g. DECADRON®), a glucocorticosteroid used to treat cancer (including multiple myeloma, leukemia, and lymphoma), inflammation, allergies, and nausea. Dexamethasone can be administered as a tablet, pill, or capsule for oral administration, or by intravenous infusion. In an embodiment, dexamethasone is administered in a combination therapy with a CD48 directed antibody-drug conjugate of the present invention. In a further embodiment, dexamethasone is administered in a combination therapy with an hMEM102 antibody-drug conjugate of the present invention. In a further embodiment, dexamethasone is administered in a combination therapy with an hMEM102-MDpr-PEG(12)-gluc-MMAE 8-load of the present invention. Dexamethasone can also be administered in a combination therapy with a CD48 directed antibody-drug conjugate of the present invention and an additional agent.

Another exemplary agent for combination therapy is cyclophosphamide (e.g. CYTOXAN®), an alkylating agent used to treat cancer (including multiple myeloma, acute myelocytic leukemia, Hodgkin's and non-Hodgkin's lymphoma, breast cancer, and lung cancer, among others). Cyclophosphamide can be administered by injection, infusion, as a tablet, pill, or capsule for oral administration, or by injection into a muscle, into the abdominal lining, or into lung lining. In an embodiment, cyclophosphamide is administered in a combination therapy with a CD48 directed antibody-drug conjugate of the present invention. In a further embodiment, cyclophosphamide is administered in a combination therapy with an hMEM102 antibody-drug conjugate of the present invention. In a further embodiment, cyclophosphamide is administered in a combination therapy with an hMEM102-MDpr-PEG(12)-gluc-MMAE 8-load of the present invention. Cyclophosphamide can also be administered in a combination therapy with a CD48 directed antibody-drug conjugate of the present invention and an additional agent.

Another exemplary agent for combination therapy is melphalan, an alkylating agent used to treat cancer (including multiple myeloma and ovarian cancer). Melphalan can be administered orally, as an injection or infusion. In an embodiment, melphalan is administered in a combination therapy with a CD48 directed antibody-drug conjugate of the present invention. In a further embodiment, melphalan is administered in a combination therapy with an hMEM102 antibody-drug conjugate of the present invention. In a further embodiment, melphalan is administered in a combination therapy with an hMEM102-MDpr-PEG(12)-gluc-MMAE 8-load of the present invention.

Melphalan can also be administered in a combination therapy with a CD48 directed antibody-drug conjugate of the present invention and an additional agent.

Another exemplary agent for combination therapy is pomalidomide (e.g. POMALYST®), an immunomodulatory agent used to treat multiple myeloma. Pomalidomide can be administered as a capsule, pill, or tablet for oral administration. In an embodiment, pomalidomide is administered in a combination therapy with a CD48 directed antibody-drug conjugate of the present invention. In a further embodiment, pomalidomide is administered in a combination therapy with an hMEM102 antibody-drug conjugate of the present invention. In a further embodiment, pomalidomide is administered in a combination therapy with an hMEM102-MDpr-PEG(12)-gluc-MMAE 8-load of the present invention.

Pomalidomide can also be administered in a combination therapy with a CD48 directed antibody-drug conjugate of the present invention and an additional agent. Pomalidomide has been combined with various additional agents to treat multiple myeloma. Pomalidomide has been combined with dexamethasone (see Richardson P et al. Pomalidomide alone or in combination with low-dose dexamethasone in relapsed and refractory multiple myeloma: a randomized phase 2 study. Blood 2014; 123:1826-1832). In an embodiment, pomalidomide is administered in a combination therapy with dexamethasone and a CD48 directed antibody-drug conjugate of the present invention. In a further embodiment, pomalidomide is administered in a combination therapy with dexamethasone and an hMEM102 antibody-drug conjugate of the present invention. In a further embodiment, pomalidomide is administered in a combination therapy with dexamethasone and an hMEM102-MDpr-PEG(12)-gluc-MMAE 8-load of the present invention.

Pomalidomide has also been combined with carfilzomib and dexamethasone (see Shah J et al. Carfilzomib, pomalidomide, and dexamethasone (CPD) in patients with relapsed and/or refractory multiple myeloma. Blood 2015; 126: 2284-2290). In an embodiment, pomalidomide is administered in a combination therapy with carfilzomib, dexamethasone, and a CD48 directed antibody-drug conjugate of the present invention. In a further embodiment, pomalidomide is administered in a combination therapy with carfilzomib, dexamethasone, and an hMEM102 antibody-drug conjugate of the present invention. In a further embodiment, pomalidomide is administered in a combination therapy with carfilzomib, dexamethasone, and an hMEM102-MDpr-PEG(12)-gluc-MMAE 8-load of the present invention.

Another exemplary agent for combination therapy is panobinostat (e.g. FARYDAK®), a histone deacetylase (HDAC) inhibitor used to treat cancer (including multiple myeloma) (see Wolf J L et al. A phase II study of oral panobinostat (LBH589) in adult patients with advanced refractory multiple myeloma. ASH Annual Meeting Abstracts, 2008). Panobinostat can be administered as a pill, capsule, or tablet for oral administration. In an embodiment, panobinostat is administered in a combination therapy with a CD48 directed antibody-drug conjugate of the present invention. In a further embodiment, panobinostat is administered in a combination therapy with an hMEM102 antibody-drug conjugate of the present invention. In a further embodiment, panobinostat is administered in a combination therapy with an hMEM102-MDpr-PEG(12)-gluc-MMAE 8-load of the present invention.

Panobinostat can also be administered in a combination therapy with a CD48 directed antibody-drug conjugate of the present invention and an additional agent. Panobinostat has been combined with various additional agents to treat multiple myeloma. For example, panobinostat has been combined with carfilzomib (see Berdeja J G et al.). In an embodiment, panobinostat is administered in a combination therapy with carfilzomib and a CD48 directed antibody-drug conjugate of the present invention. In a further embodiment, panobinostat is administered in a combination therapy with carfilzomib and an hMEM102 antibody-drug conjugate of the present invention. In a further embodiment, panobinostat is administered in a combination therapy with carfilzomib and an hMEM102-MDpr-PEG(12)-gluc-MMAE 8-load of the present invention. Panobinostat has also been combined with bortezomib and dexamethasone (see Richardson P et al. 2013). In an embodiment, panobinostat is administered in a combination therapy with bortezomib, dexamethasone, and a CD48 directed antibody-drug conjugate of the present invention. In a further embodiment, panobinostat is administered in a combination therapy with bortezomib, dexamethasone, and an hMEM102 antibody-drug conjugate of the present invention. In a further embodiment, panobinostat is administered in a combination therapy with bortezomib, dexamethasone, and an hMEM102-MDpr-PEG(12)-gluc-MMAE 8-load of the present invention.

Another exemplary agent for combination therapy is ixazomib (NINLARO®), a proteasome inhibitor used to treat cancer (including multiple myeloma). Ixazomib can be administered orally. In an embodiment, ixazomib is administered in a combination therapy with a CD48 directed antibody-drug conjugate of the present invention. In a further embodiment, ixazomib is administered in a combination therapy with an hMEM102 antibody-drug conjugate of the present invention. In a further embodiment, ixazomib is administered in a combination therapy with an hMEM102-MDpr-PEG(12)-gluc-MMAE 8-load of the present invention. Ixazomib can also be administered in a combination therapy with a CD48 directed antibody-drug conjugate of the present invention and an additional agent. Ixazomib has been combined with various additional agents to treat multiple myeloma. For example, ixazomib has been combined with lenalidomide and dexamethasone (see Moreau P et al. Ixazomib, an investigational oral proteasome inhibitor, in combination with lenalidomide and dexamethasone, significantly extends progression-free survival for patients with relapsed and/or refractory multiple myeloma: the phase 3 tourmaline-MM1 study. ASH Annual Meeting Abstracts, 2015). In an embodiment, ixazomib is administered in a combination therapy with lenalidomide, dexamethasone, and a CD48 directed antibody-drug conjugate of the present invention. In a further embodiment, ixazomib is administered in a combination therapy with lenalidomide, dexamethasone, and an hMEM102 antibody-drug conjugate of the present invention. In a further embodiment, ixazomib is administered in a combination therapy with lenalidomide, dexamethasone, and an hMEM102-MDpr-PEG(12)-gluc-MMAE 8-load of the present invention.

Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

The following examples are offered to illustrate, but not to limit the claimed invention.

Example 1: Antibody Selection and Humanization

The murine MEM102 antibody binds to the human CD48 protein and was first disclosed in Bazil et al., *Folia Biologica* 35:289-297 (1989). Nucleic acids encoding the murine MEM102 antibody were sequenced and encoded heavy and light chain CDR sequences were identified, i.e., SEQ ID NO:3-8. Several humanized MEM102 antibodies were constructed using the hIgG VH7-4-1/hIgG-JH5 heavy chain variable region human germline and the hIgG-VK6-21/hIgG-JK4 light chain variable region human germline as the human acceptor sequences. The antibodies differed in the selection of amino acid residues to be mutated back to the mouse antibody or mouse germline sequence. The antibody designated HALA (heavy chain as set forth in SEQ ID NO:1 (vHA) and the light chain as set forth in SEQ ID NO:2 (vLA) was selected as the lead humanized MEM102 antibody on the basis of its (i) binding characteristics, (ii) ability to deliver drug and (iii) number of back mutations as compared to the other variants. Humanized MEM102 antibody is also referred to as hMEM102.

Antibodies designated HCLA (antibody having the heavy chain variable region designated vHC and the light chain variable region designated vLA), HALB (antibody having the heavy chain variable region designated vHA and the light chain variable region designated vLB), HBLA (antibody having the heavy chain variable region designated vHB and the light chain variable region designated vLA), HBLB (antibody having the heavy chain variable region designated vHB and the light chain variable region designated vLB), HCLB (antibody having the heavy chain variable region designated vHC and the light chain variable region designated vLB) can be used in the present invention in place of the HALA antibody. See FIGS. 1 and 2 for the vHA, vHB, vHC, vLA, vLB, and vLC sequences. The binding affinities for the various humanized forms of MEM102 are similar whether tested against cells overexpressing human or cyno CD48.

Example 2: hMEM102 Binding Characteristics

Methods:
To determine saturation binding of anti-CD48 antibodies, human U-266 multiple myeloma tumor cells or cynomolgus monkey CD48 stably transfected CHO-DG44 clonal cells were stained with titrated Alexa Fluor-647 conjugated antibody (0.8 ng/ml-50 μg/mL) loaded with approximately 2-4 fluorophores per antibody. After one hour incubation on ice, cells were washed twice with phosphate buffered saline containing 2% fetal bovine serum and 0.02% sodium azide. Fluorescence was detected on a LSRII flow cytometer and Kd values were determined using one-site binding (hyperbola) non-linear regression in GraphPad Prism.

Figure 3:
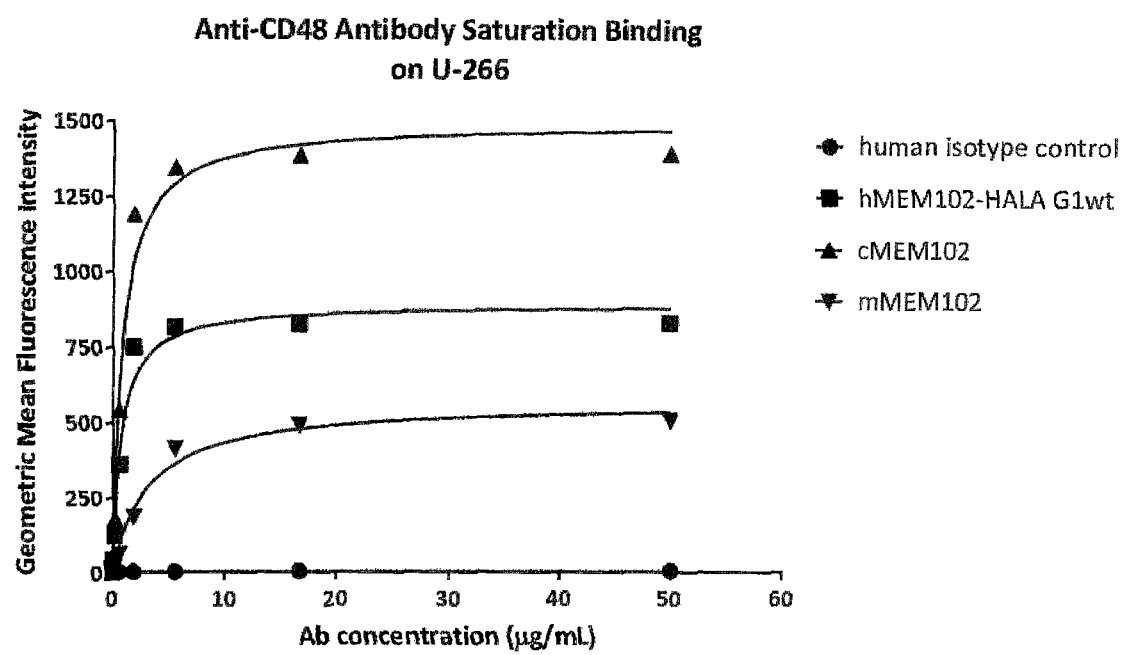
FIG. 3 shows saturation binding curves for MEM102 antibodies on human U-266 multiple myeloma cells.
Figure 4:
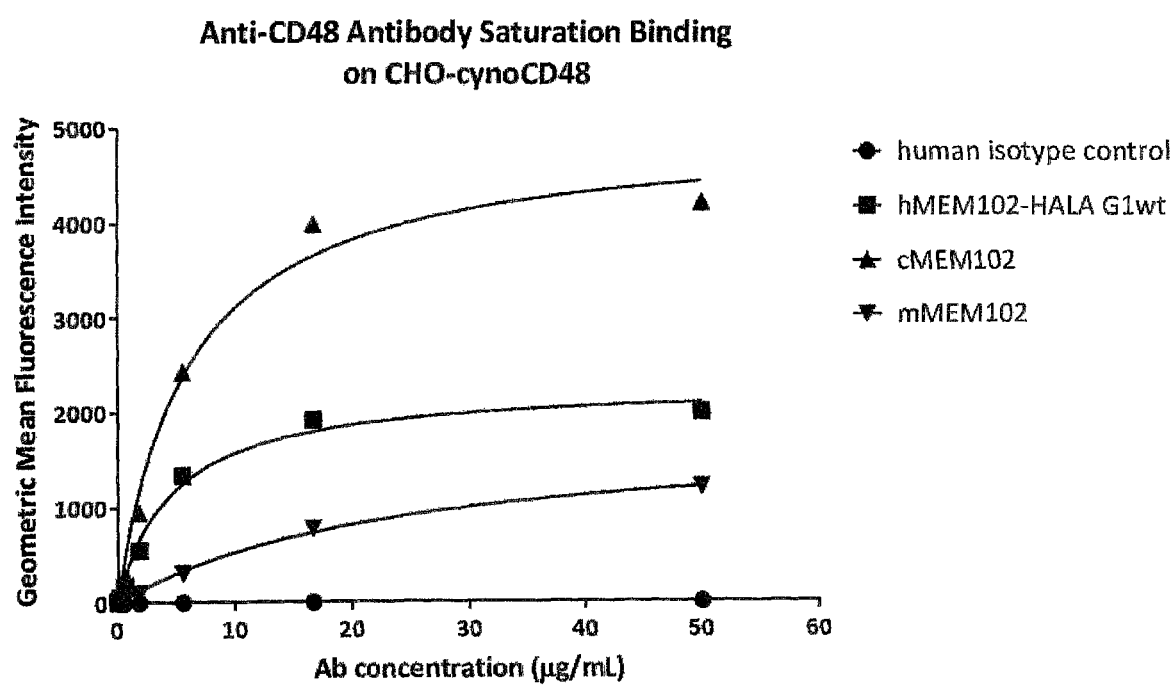
FIG. 4 shows saturation binding curves for MEM102 antibodies on CHO cells transfected with cynomolgus monkey CD48.

Results:

Table 1 and FIGS. 3 and 4 show that hMEM102-HALA antibody has similar binding affinity compared to cMEM102 in U-266 cells, as indicated by the low Kd values. Binding affinity of hMEM102-HALA and cMEM102 to cynomolgus monkey CD48 in stably transfected CHO-DG44 clonal cells was also comparable. Both hMEM102-HALA and cMEM102 have greater than 4-fold lower Kd compared to mMEM102 in both cell lines. The anti-CD48 antibodies had approximately 6-fold stronger binding affinity to human CD48 compared to cynomolgus monkey CD48.

TABLE 1

| Antibody | Lot# | Kd (nM) U-266 | Kd (nM) CHO-DG44-cynomolgus monkey CD48 |
|---|---|---|---|
| hMEM102-HALA | 9915029F | 5.0 | 31.1 |
| cMEM102 | 7713039A | 5.8 | 40.5 |
| mMEM102 | 275036T | 20.8 | 164.7 |

Example 3: Synthesis of MDpr-PEG(12)-glyc-MMAE and Conjugation to hMEM102

General Information.

All commercially available anhydrous solvents were used without further purification. PEG reagents were obtained from Quanta BioDesign (Powell, Ohio). Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Column chromatography was performed on a Biotage Isolera One flash purification system (Charlotte, N.C.). Analytical HPLC was performed on a Varian ProStar 210 solvent delivery system configured with a Varian ProStar 330 PDA detector. Samples were eluted over a C12 Phenomenex Synergi 2.0×150 mm, 4 μm, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass mass spectrometer interfaced to an HP Agilent 1100 HPLC instrument equipped with a C12 Phenomenex Synergi 2.0×150 mm, 4 μm, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2 Tof mass spectrometer interfaced to a Waters 2695 Separations Module with a Waters 2996 Photodiode Array Detector; the column, mobile phases, gradient, and flow rate were same as for LC-MS system 1. UPLC-MS was carried out on a Waters SQ mass detector interfaced to an Acquity Ultra Performance LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.5 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 μm, 80 Å reverse phase column eluting with 0.1% formic acid in water (solvent A) and 0.1% formic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm. Preparative HPLC for compounds in Schemes 3 and 4 was carried out with 0.1% trifluoroacetic acid in both mobile phases, instead of 0.1% formic acid.

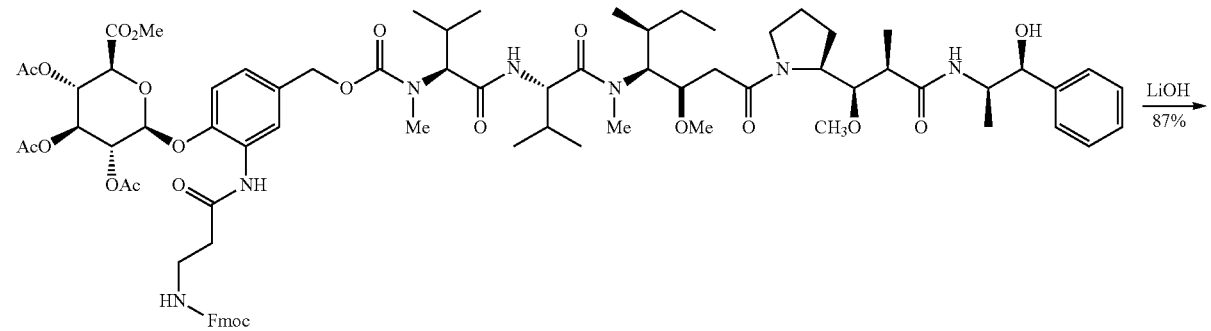

Scheme 1.

1 (compound 8a in US 2008/0241128 A1)

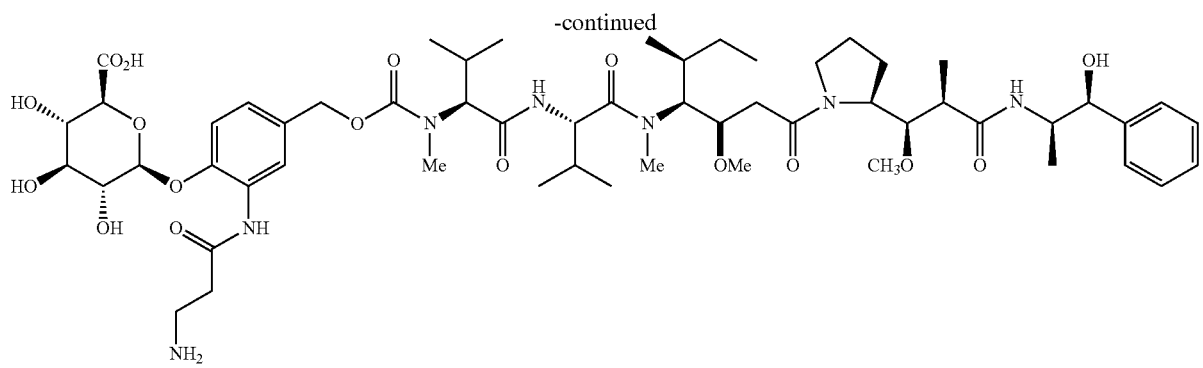

2

(2S,3S,4S,5R,6S)-6-(2-(3-aminopropanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (2)

To a flask containing the known (compound 8a in US 2008/0241128 A1) glucuronide-MMAE intermediate 2 (40 mg, 26.8 μmol) was added 0.9 mL methanol and 0.9 mL tetrahydrofuran. The solution was then cooled in an ice bath and lithium hydroxide monohydrate (6.8 mg, 161 μmol) was added drop wise in as a solution in 0.9 mL water. The reaction was then stirred on ice for 1.5 h, at which time LC/MS revealed complete conversion to product. Glacial acetic acid (9.2 μL, 161 μmol) was then added and the reaction was concentrated to dryness. Preparative HPLC afforded the fully deprotected glucuronide-MMAE linker intermediate 3 (26 mg, 87%) as an oily residue. Analytical HPLC (0.1% formic acid): $t_R$ 9.3 min. LC-MS system 1: $t_R$ 11.10 min, m/z (ES$^+$) found 1130.48 (M+H)$^+$, m/z (ES$^-$) found 1128.63 (M−H)$^-$.

Scheme 2.

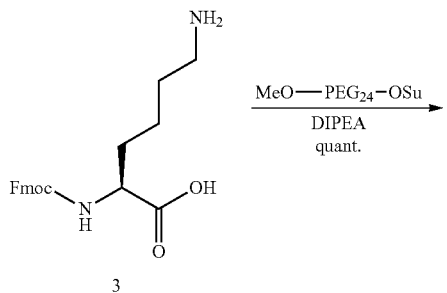

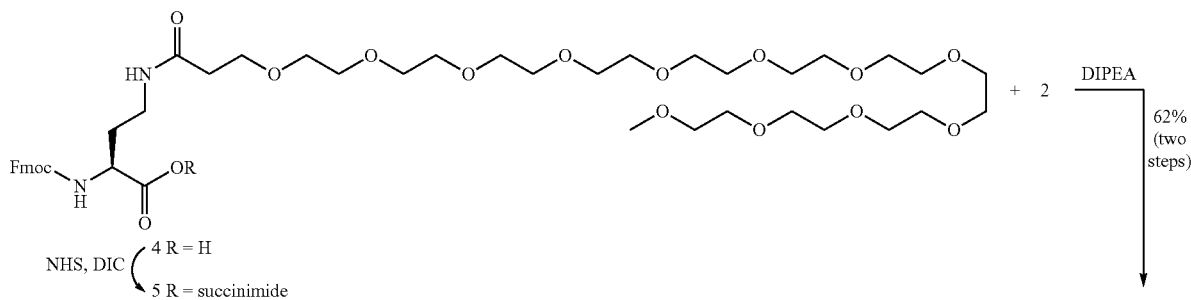

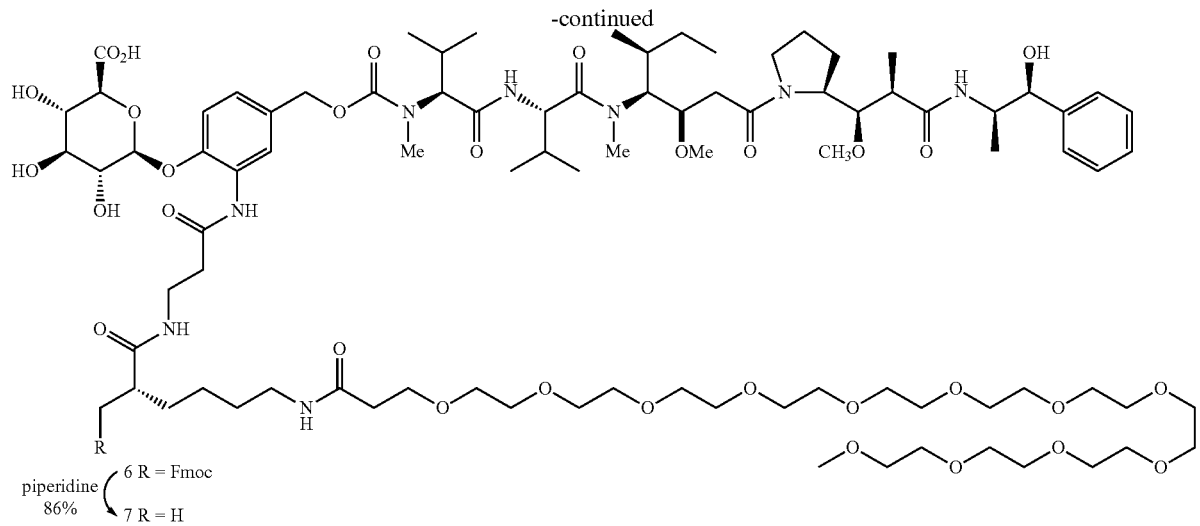

(S)-44-((((9H-fluoren-9-yl)methoxy)carbonyl) amino)-38-oxo-2,5,8,11,14,17,20,23,26,29,32,35-dodecaoxa-39-azapentatetracontan-45-oic acid (4)

To a flask containing N$_\alpha$-Fmoc-lysine 3 (59 mg, 161 μmol) was added 2.9 mL anhydrous dichloromethane, followed by methoxy-PEG12-OSu (100 mg, 146 μmol). DIPEA (127 μL, 730 μmol) was then added and the reaction was stirred under nitrogen at room temperature and followed by TLC and LC/MS. After 2 h, LC/MS revealed conversion to product. The reaction solution was diluted in dichloromethane and purified by silica gel chromatography. The stationary phase was eluted with dichloromethane with increasing amounts of methanol (0% to 20%) to provide the desired product 4 (153 mg, 112%). UPLC-MS: $t_R$ 1.77 min, m/z (ES$^+$) found 939.58 (M+H)$^+$.

(S)-2,5-dioxopyrrolidin-1-yl 44-((((9H-fluoren-9-yl) methoxy)carbonyl)amino)-38-oxo-2,5,8,11,14,17,20, 23,26,29,32,35-dodecaoxa-39-azapentatetracontan-45-oate (5)

A flask was charged with N$_\alpha$-Fmoc-lysine(PEG12)-OH 4 (153 mg, 163 μmol) and 1.6 mL anhydrous tetrahydrofuran. N-hydroxysuccinimide (28 mg, 245 μmol) was added, followed by diisopropylcarbodiimide (38 μL, 245 μmol). The reaction was sealed under nitrogen and stirred overnight. The crude reaction was diluted in dichloromethane and pure over silica gel eluted with dichloromethane with increasing amounts of methanol (0% to 10%) to provide the desired activated ester 5 (155 mg). The material was carried forward without further characterization. UPLC-MS: $t_R$ 1.92 min, m/z (ES$^+$) found 1036.48 (M+H)$^+$.

(2S,3S,4S,5R,6S)-6-(2-((S)-44-((((9H-fluoren-9-yl) methoxy)carbonyl)amino)-38,45-dioxo-2,5,8,11,14, 17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (6)

Deprotected glucuronide-MMAE linker intermediate 2 (92 mg, 81 μmol) was dissolved in anhydrous dimethylformamide (1.6 mL) and added to a flask containing Nα-Fmoc-lysine(PEG12)-OSu 5 (101 mg, 97 μmol). Diisopropylethylamine (70 μL, 405 μmol) was then added, the reaction was then stirred under nitrogen at room temperature. After 4.5 h, LC-MS revealed conversion to product. The product was purified by preparative HPLC to provide Fmoc-Lys (PEG12)-glucuronide-MMAE intermediate 6 (111 mg, 62% over two steps) as an oily residue. UPLC-MS: $t_R$ 2.01 min, m/z (ES$^+$) found 2050.92 (M+H)$^+$.

(2S,3S,4S,5R,6S)-6-(2-((S)-44-amino-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5, 8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (7)

Fmoc-Lys(PEG12)-glucuronide-MMAE intermediate 6 (111 mg, 54 μmol) was dissolved in 2.2 mL anhydrous dimethylformamide, followed by addition of 0.5 mL of piperidine. The reaction was stirred under nitrogen for 3 hours and then concentrated to dryness. The product was purified by preparative HPLC to provide H-Lys(PEG12)-glucuronide-MMAE intermediate 7 (85 mg, 86%) as an oily residue. UPLC-MS: $t_R$ 1.50 min, m/z (ES$^+$) found 1829.31 (M+H)$^+$.

(S)-2,5-dioxopyrrolidin-1-yl 3-((tert-butoxycarbonyl)amino)-2-(2,5-dioxo-2,5-dihydro-1H-pyrrol-1-yl)propanoate (9)

(S)—N$_\alpha$-maleimido-N$_\beta$-Boc-diaminopropanoic acid 8 (*Nature Biotechnology*, 2014, 32, 1059-1062) (400 mg, 1.4 mmol) was dissolved in 7 mL anhydrous dimethylformamide. N-hydroxysuccinimide (178 mg, 1.5 mmol) was added, followed by 1-ethyl-3-(3-dimethylaminopropyl) carbodiimide (298 mg, 1.5 mmol). The reaction was stirred at room temperature under nitrogen for 3 hours. Aqueous workup was achieved through dilution into 120 mL water;

the aqueous layer was then extracted three times with 60 mL ethyl acetate. The combined organic layer was then washed with brine, dried over sodium sulfate, and concentrated to dryness. The product was purified by flash column chromatography, eluting mixtures of hexanes:ethyl acetate (50:50 to 0:100) to provide (S)—$N_\alpha$-maleimido-$N_\beta$-Boc-diaminopropanoic acid NHS ester [MDpr(Boc)-OSu] 9 (297 mg, 55%). LC-MS system 1: $t_R$ 12.23 min, m/z (ES$^+$) found 282.0599 (M+H-Boc group)$^+$. LC-MS system 2: $t_R$ 11.30 min, m/z (ES$^+$) found 2580.2515 (M+H)$^+$.

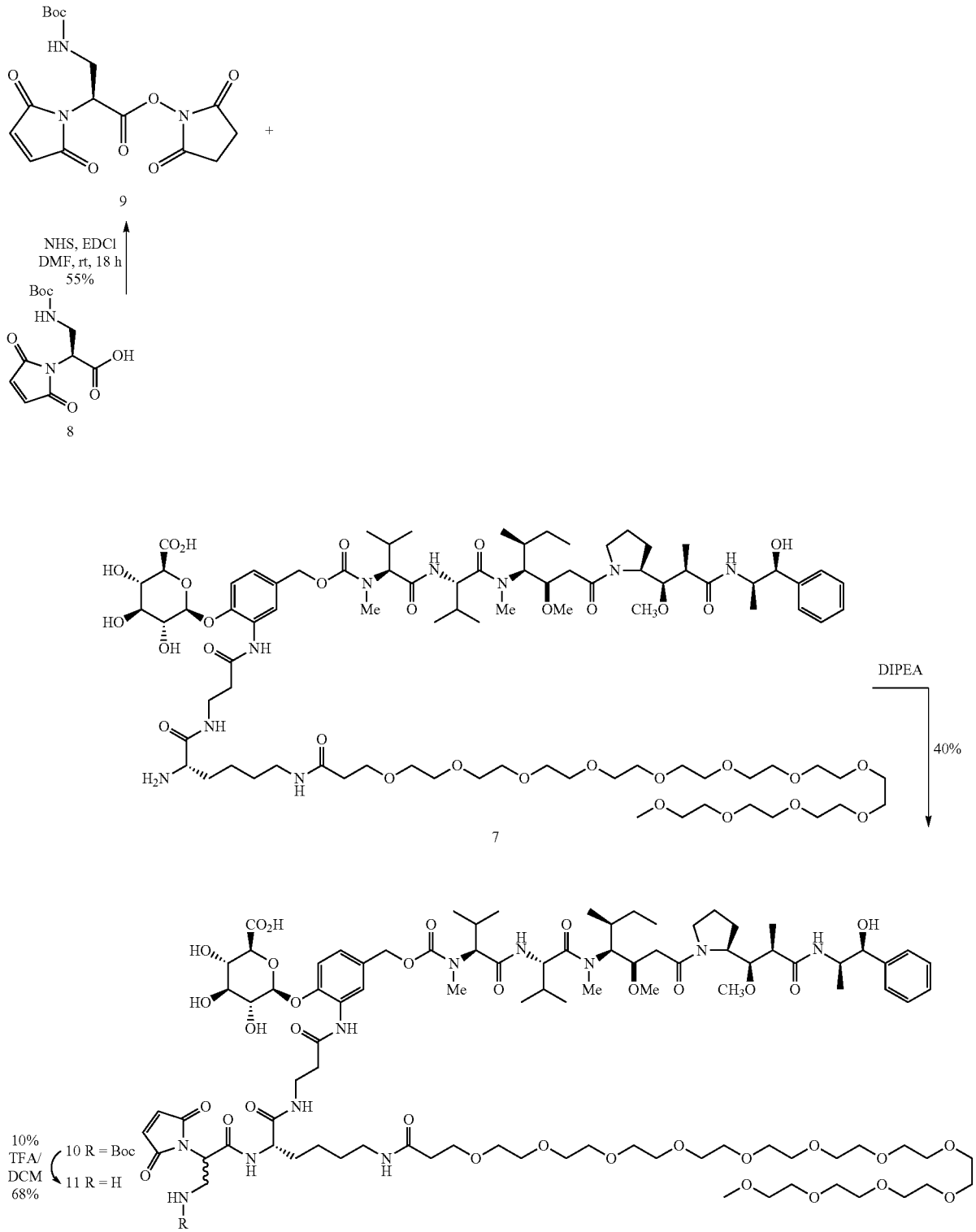

(2R/S,3S,4S,5R,6S)-6-(2-((S)-44-((S)-3-((tert-bu-toxycarbonyl)amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (10)

MDpr(Boc)-OSu 9 (20 mg, 53 µmol) was dissolved in 2.2 mL of anhydrous dimethylformamide and added to a flask containing H-Lys(PEG12)-glucuronide-MMAE linker intermediate 7 (86 mg, 44 µmol). Diisopropylethylamine (15 µL, 88 µmol) was then added, the reaction was then stirred under nitrogen at room temperature for 2.5 h. The reaction was quenched with 15 µL glacial acetic acid and purified by preparative HPLC to afford MDpr(Boc)-Lys(PEG12)-glucuronide-MMAE intermediate 10 (37 mg, 40%), as a mixture of diastereomers. The diastereomers were separable by chiral chromatography. UPLC-MS: $t_R$ 1.84 min, m/z (ES$^+$) found 2095.44 (M+H)$^+$.

(2R/S,3S,4S,5R,6S)-6-(2-((S)-44-((R)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (11)

A flask containing MDpr(Boc)-Lys(PEG12)-glucuronide-MMAE intermediate 10 (34 mg, 16 umol) was cooled to 0° C. in an ice bath under nitrogen. A solution of 10% trifluoroacetic acid in dichloromethane (0.8 mL) was added dropwise. The reaction was then stirred at 0° C. for 2 h, at which time LC-MS revealed complete Boc deprotection. The reaction was then concentrated to a crude residue and purified by preparative HPLC to provide MDpr-Lys(PEG12)-glucuronide-MMAE linker 11 (22 mg, 68%). UPLC-MS: $t_R$ 1.50 min, m/z (ES$^+$) found 1995.18 (M+H)$^+$.

Compound 11 was conjugated via its interchain thiols to the anti-CD48 antibody at an average drug loading of 8 drugs per antibody using methods known in the art (see, for example, U.S. Pat. No. 7,659,241).

Example 4: Cytotoxicity of hMEM-102 ADCs on Multiple Myeloma Cancer Cell Lines

Methods:

Human multiple myeloma cell lines EJM (DSMZ; IMDM+20% FBS), L363 (DSMZ; RPMI 1640+15% FBS), MM.1R (ATCC; RPMI 1640+10% FBS), NCI-H929 (ATCC: RPMI 1640+10% FBS), U-266 (ATCC; RPMI 1640+15% FBS), and LP-1 (DSMZ; IMDM+20% FBS) were cultured at 37° C., 5% $CO_2$. Anti-CD48 auristatin antibody drug conjugates were serially diluted 3-fold in media to produce 10 point dose curves (1,000 ng/mL-0.05081 ng/mL) and applied to multiple myeloma cells cultured in 96-well assay plates (10,000 to 15,000 cells per well in 200 µL media). Cells were incubated with ADCs for 96 hours total at 37° C., 5% CO2. Cell viability was assayed using the Cell Titer Glo luminescent cytotoxicity assay (Promega), and data collected using an EnVision plate reader (PerkinElmer). All cytotoxicity assays were performed with quadruplicate data points and the mean IC50 values from 2-3 independent experiments are reported.

Apoptotic cell death was measured using the Caspase-Glo 3/7 assay (Promega), using identical assay conditions as described above.

Results:

Results are shown in Table 2. The hMEM102 antibody was conjugated to vcMMAE(4-load), mcMMAF(4-load), and MDpr-PEG(12)-gluc-MMAE, as an eight load, also referred to as hMEM102-5088(8). Similar conjugations were performed on a control antibody, a non-CD48 binding antibody. hMEM102-5088(8) exhibited improved cytotoxic activity as compared to the same antibody conjugated to vcMMAE(4) and mcMMAF(4). As a negative control, a cell line that does not express CD48, LP-1, was also included.

TABLE 2

| | | | Multiple Myeloma Cell Lines (# CD48 receptors/cell) | | | | | |
|---|---|---|---|---|---|---|---|---|
| Antibody | Drug Linker | Drug Load | EJM (135,000) | L363 (460,000) | MM.1R (336,000) | NCI-H929 (483,000) | U-266 (270,000) | LP-1 (0) |
| hMEM102 | vcMMAE | 4 | 8.7 | 36 | 12 | 13 | 6.0 | >1000 |
| hMEM102 | mcMMAF | 4 | 4.0 | 34 | 7.0 | Not tested | 3.0 | >1000 |
| hMEM102 | MDpr-PEG(12)-gluc-MMAE | 8 | 2.0 | 11 | 2.0 | 2.5 | 1.0 | >1000 |
| hMEM102 | Auristatin T | 8 | 1.0 | 15 | 1.7 | 1.5 | 1.0 | >1000 |
| hIgG | vcMMAE | 4 | >1000 | >1000 | >1000 | >1000 | >1000 | >1000 |
| hIgG | mcMMAF | 4 | >1000 | >1000 | >1000 | >1000 | >1000 | >1000 |
| hIgG | MDpr-PEG(12)-gluc-MMAE | 8 | >1000 | >1000 | >1000 | >1000 | >1000 | >1000 |
| hIgG | Auristatin T | 8 | >1000 | >1000 | >1000 | >1000 | >1000 | >1000 |

Figure 5:
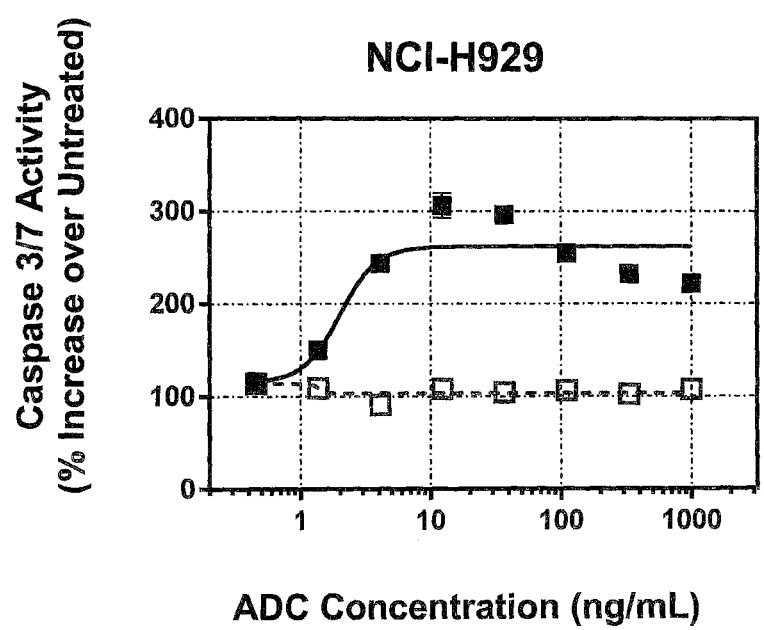
FIG. 5 shows caspase 3/7 activation (apoptotic cell death) in human NCI-H929 multiple myeloma cells after treatment with MEM-102 ADCs.
Figure 6:
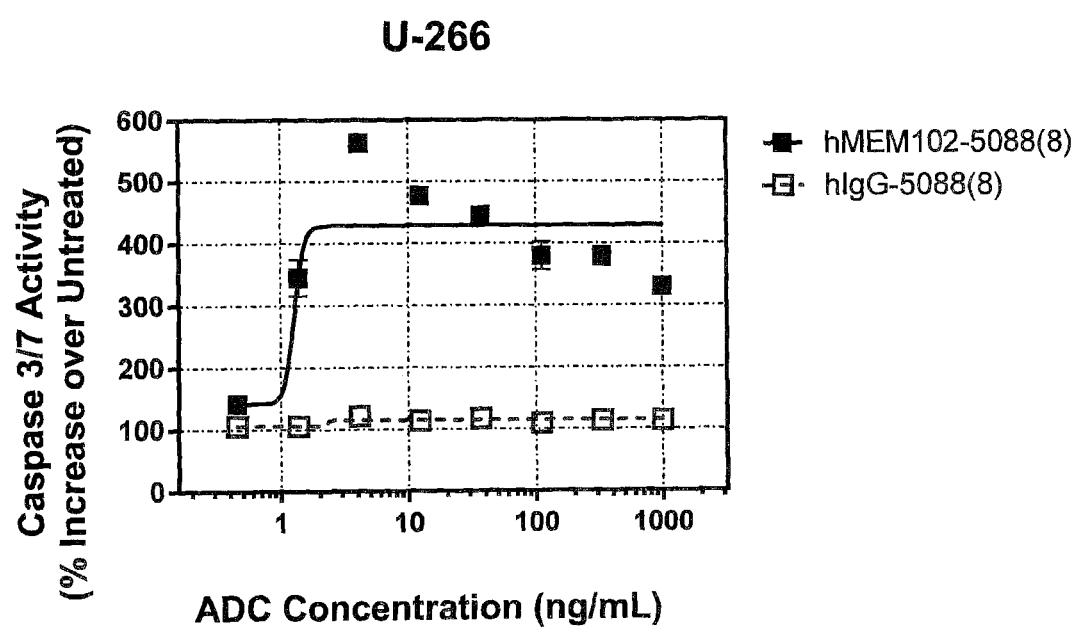
FIG. 6 shows caspase 3/7 activation in human U-266 multiple myeloma cells after treatment with MEM-102 ADCs.

Two cell lines were assessed for apoptotic cell death, NCI-H929 and U-266. Results are shown in FIGS. 5 and 6. In both cell lines, the hMEM102-MDpr-PEG(12)-gluc-MMAE (8) conjugate induced apoptotic cell death after seventy hours of exposure to the drug. No apoptotic death was seen in cells treated with a control antibody conjugated to MDpr-PEG(12)-gluc-MMAE (8). In the Figure the drug linker is referenced as 5088 and eight drug linkers are conjugated per antibody. In both FIGS. 5 and 6, the hMEM102-MDpr-PEG(12)-gluc-MMAE (8) conjugate is represented by filled squares, while the control antibody-MDpr-PEG(12)-gluc-MMAE (8) conjugate is represented by open squares.

Example 5: In Vivo Multiple Myeloma Xenograft Studies

Figure 7:
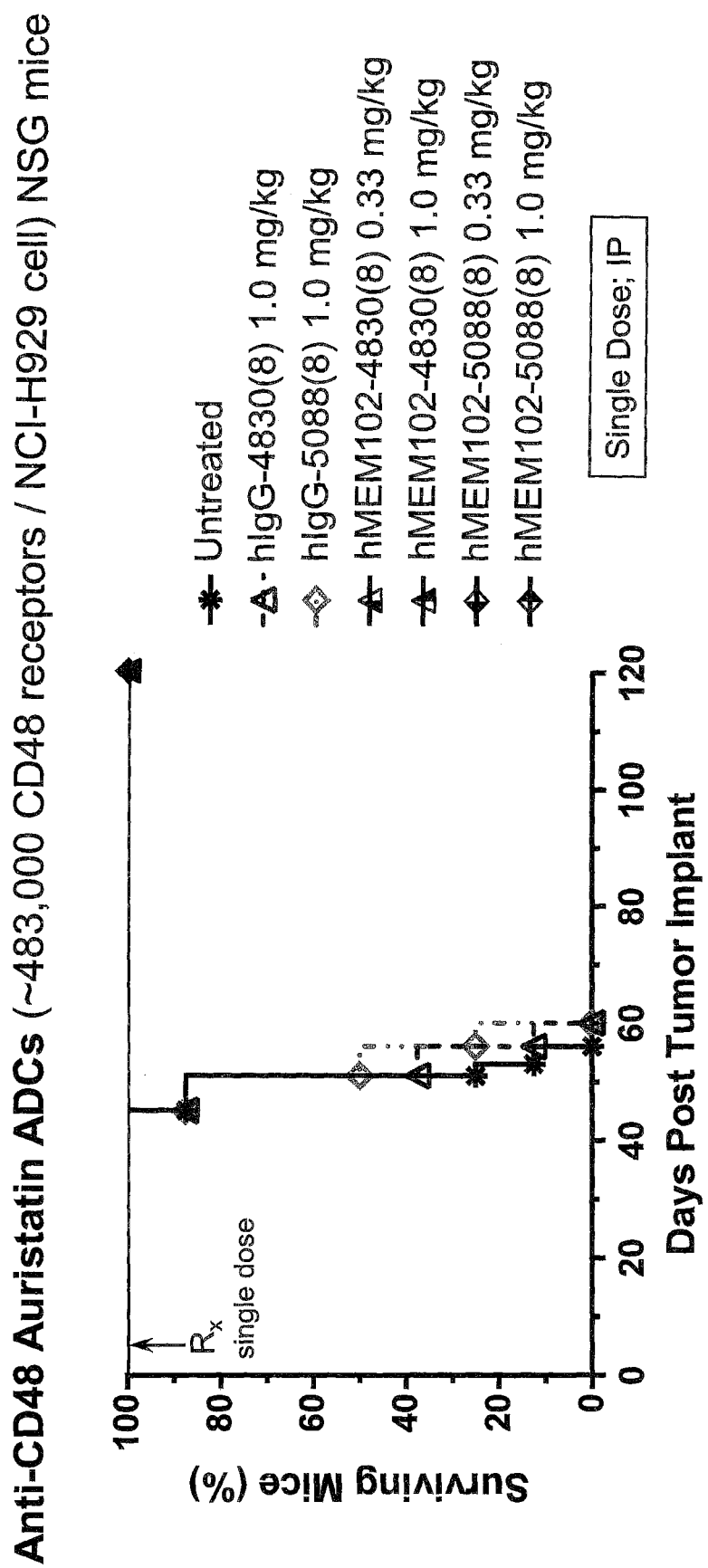
FIG. 7 shows in vivo activity of hMEM102 ADCs in a mouse xenograft model implanted with NCI-H929 cells. This is a disseminated model of multiple myeloma.

Female NSG (NOD scid gamma; NOD.Cg-Prkdc$^{scid}$ Il2rg$^{tm1Wjl}$/SzJ) mice were implanted with 2.5 million NCI-H929 cells, per animal intravenously to generate a disseminated model of multiple myeloma. Five days after tumor cell implant, n=8 mice per treatment group were given a single intraperitoneal injection hMEM102-MDpr-PEG(12)-gluc-MMAE (5088) ADC or non-binding control hIgG-MDpr-PEG(12)-gluc-MMAE (5088) ADC or hMEM102-Auristatin T (4830) or non-binding control hIgG-Auristatin T (4830). ADC dose levels examined were 0.33 mg/kg and 1.0 mg/kg. Mice with advanced tumor burden were sacrificed upon showing symptoms of hind limb paralysis, cranial swelling, and/or moribundity. As shown in FIG. 7, both ADCs produced durable complete responses in 8/8 mice at all dose levels (single dose), while non-binding control ADC dosed mice were all sacrificed due to disease by day-60 of the study.

Figure 8:
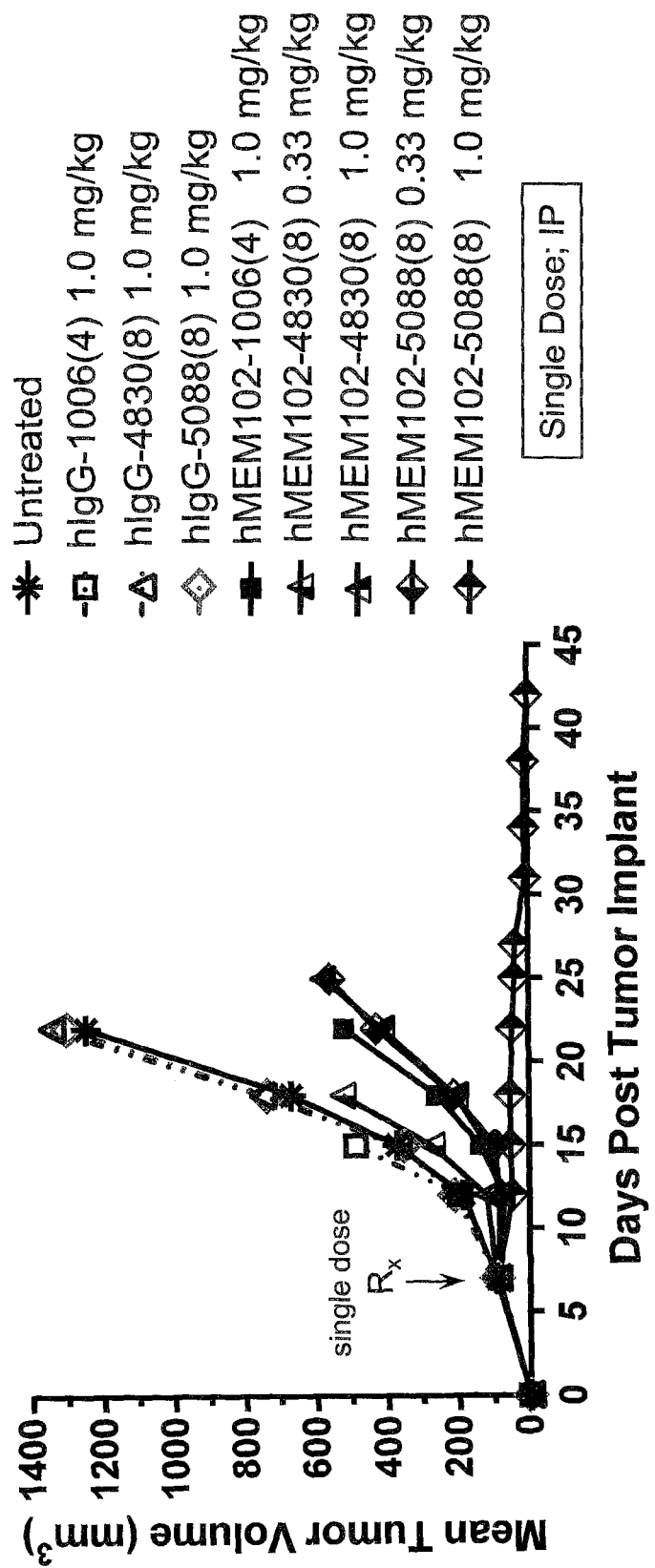
FIG. 8 shows in vivo activity of hMEM102 ADCs in a mouse xenograft model implanted with NCI-H929 cells. This is a subcutaneous model of multiple myeloma.

Female NSG (NOD scid gamma; NOD.Cg-Prkdc$^{scid}$ Il2rg$^{tm1Wjl}$/SzJ) mice were implanted with 1 million NCI-H929 multiple myeloma cells per animal subcutaneously. When mean tumor volume reached 100 mm$^3$, n=7 mice per treatment group were given a single intraperitoneal injection of hMEM102-MDpr-PEG(12)-gluc-MMAE (5088) ADC or non-binding control hIgG-MDpr-PEG(12)-gluc-MMAE (5088) ADC or hMEM102-Auristatin T (4830) or non-binding control hIgG-Auristatin T (4830), or hMEM102-vcMMAE (1006) ADC or non-binding control hIgG-vcMMAE (1006). ADC dose levels examined were 0.33 mg/kg and 1.0 mg/kg. Individual mice were sacrificed when subcutaneous NCI-H929 tumor volume reached 1,000 mm$^3$. As shown in FIG. 8, the of hMEM102-MDpr-PEG(12)-gluc-MMAE (5088) ADC produced durable complete responses in all mice at the 1.0 mg/kg dose levels. At the lower dose level of 0.33 mg/kg, hMEM102-MDpr-PEG(12)-gluc-MMAE (5088) produced a tumor delay. The vcMMAE and Auristatin T ADCs induced tumor delay only at the highest doses.

Figure 9:
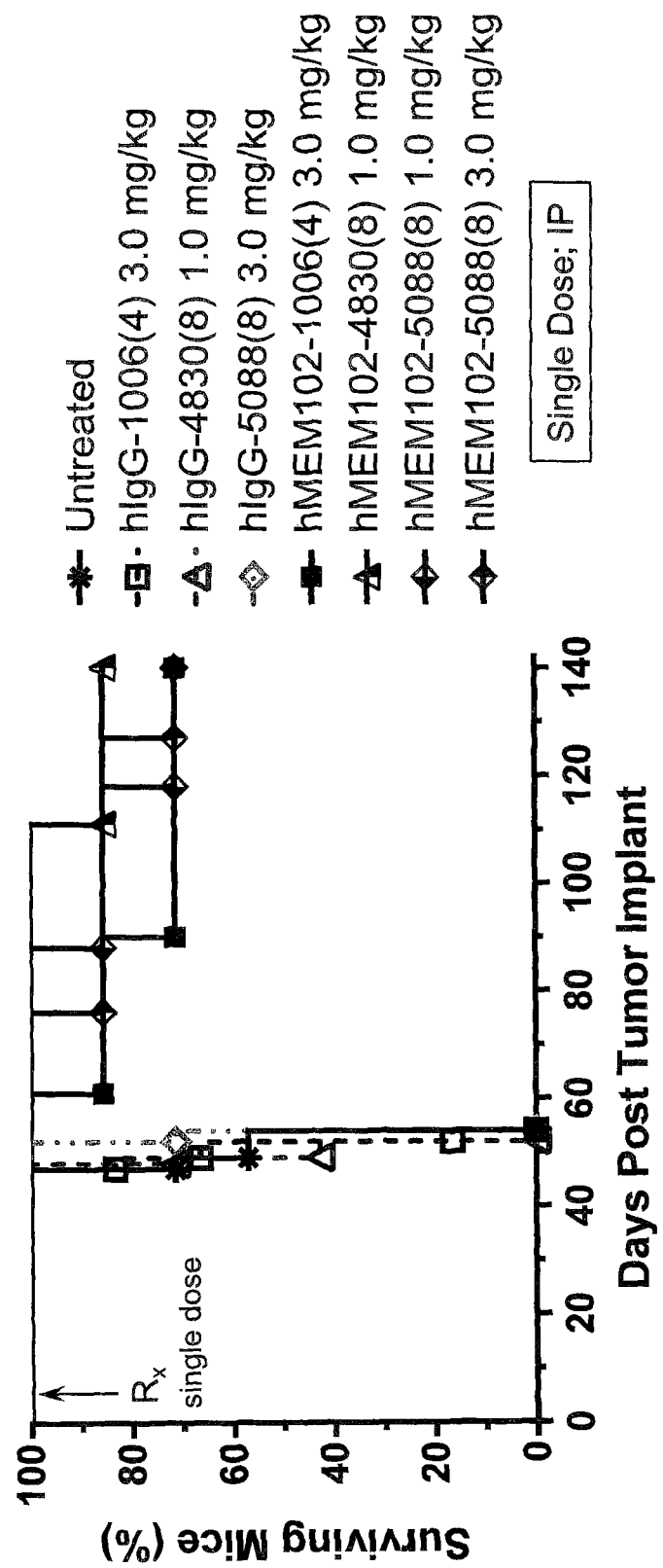
FIG. 9 shows in vivo activity of hMEM102 ADCs in a mouse xenograft model implanted with MM.1R cells. This is a disseminated model of multiple myeloma.

Female NSG (NOD scid gamma; NOD.Cg-Prkdc$^{scid}$Il2rg$^{tm1Wjl}$/SzJ) mice were implanted with 1 million MM.1R cells, per animal intravenously to generate a disseminated model of multiple myeloma. Five days after tumor cell implant, n=7 mice per treatment group were given a single intraperitoneal injection hMEM102-MDpr-PEG(12)-gluc-MMAE (5088) ADC or non-binding control hIgG-MDpr-PEG(12)-gluc-MMAE (5088) ADC or hMEM102-Auristatin T (4830) or non-binding control hIgG-Auristatin T (4830). ADC dose levels examined were 1.0 mg/kg and 3.0 mg/kg. Mice with advanced tumor burden were sacrificed upon showing symptoms of hind limb paralysis, cranial swelling, and/or moribundity. As shown in FIG. 9, both ADCs produced durable complete responses in mice at all dose levels tested (single dose), while non-binding control ADC dosed mice were all sacrificed due to disease by day-60 of the study.

Figure 10:
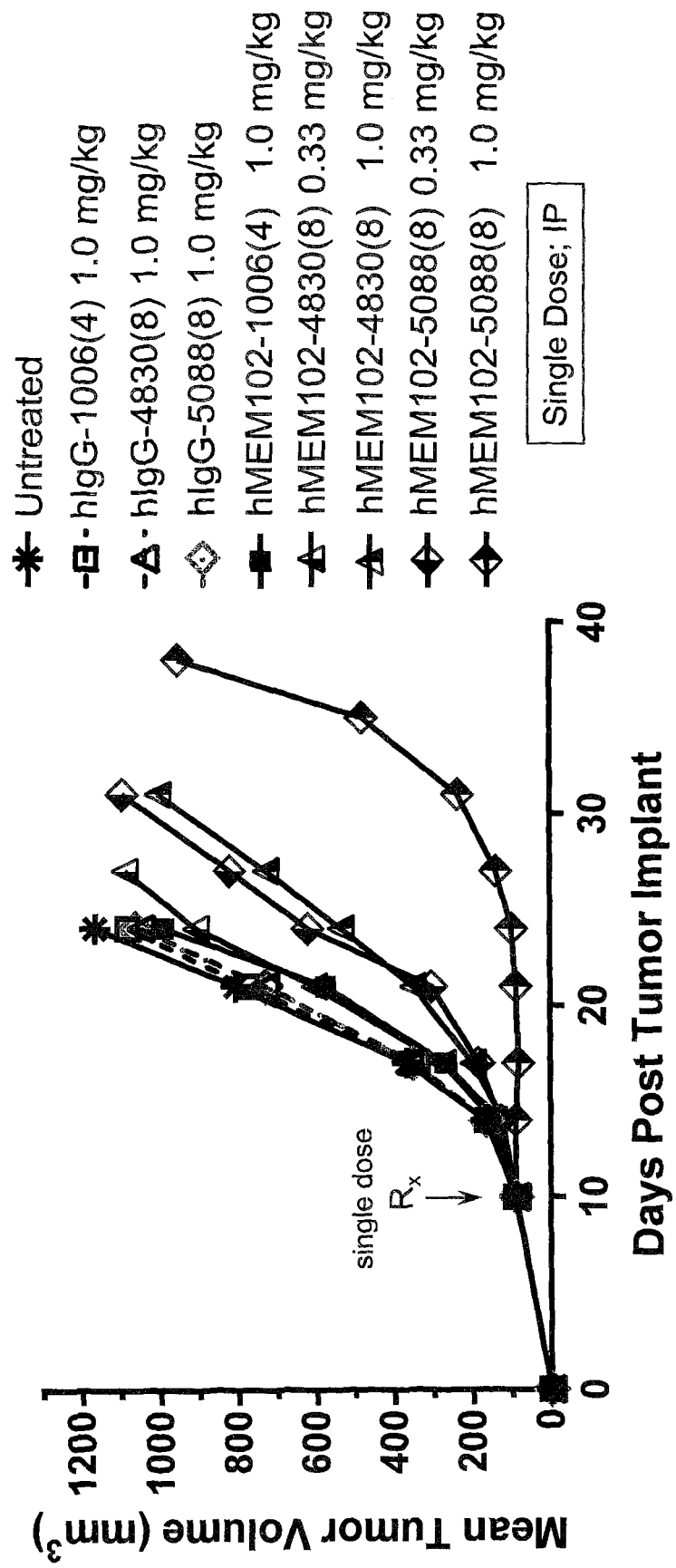
FIG. 10 shows in vivo activity of hMEM102 ADCs in a mouse xenograft model implanted with MM.1R cells. This is a subcutaneous model of multiple myeloma.

Female NSG (NOD scid gamma; NOD.Cg-Prkdc$^{scid}$ Il2rg$^{tm1Wjl}$/SzJ) mice were implanted with 5 million MM.1R multiple myeloma cells per animal subcutaneously. When mean tumor volume reached 100 mm$^3$, n=7 mice per treatment group were given a single intraperitoneal injection of hMEM102-MDpr-PEG(12)-gluc-MMAE (5088) ADC or non-binding control hIgG-MDpr-PEG(12)-gluc-MMAE (5088) ADC or hMEM102-Auristatin T (4830) or non-binding control hIgG-Auristatin T (4830), or hMEM102-vcMMAE (1006) ADC or non-binding control hIgG-vcMMAE (1006). ADC dose levels examined were 0.33 mg/kg and 1.0 mg/kg. Individual mice were sacrificed when subcutaneous MM.1R tumor volume reached 1,000 mm$^3$. As shown in FIG. 10, the of hMEM102-MDpr-PEG(12)-gluc-MMAE (5088) ADC produced the most potent antitumor response and the longest tumor delay.

Figure 11:
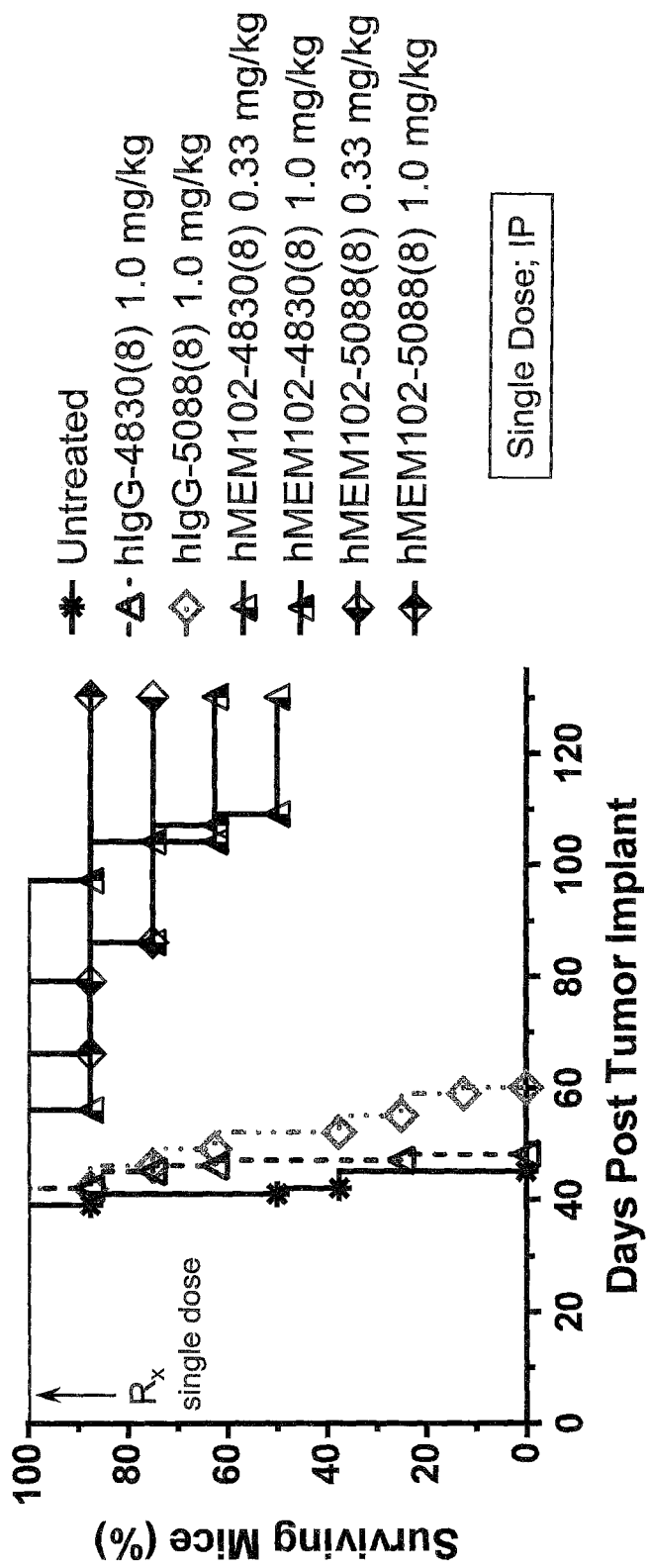
FIG. 11 shows in vivo activity of hMEM102 ADCs in a mouse xenograft model implanted with EJM cells. This is a disseminated model of multiple myeloma.

Female NSG (NOD scid gamma; NOD.Cg-Prkdc$^{scid}$ Il2rg$^{tm1Wjl}$/SzJ) mice were implanted with 5 million EJM cells, per animal intravenously to generate a disseminated model of multiple myeloma. Five days after tumor cell implant, n=8 mice per treatment group were given a single intraperitoneal injection hMEM102-MDpr-PEG(12)-gluc-MMAE (5088) ADC or non-binding control hIgG-MDpr-PEG(12)-gluc-MMAE (5088) ADC or hMEM102-Auristatin T (4830) or non-binding control hIgG-Auristatin T (4830). ADC dose levels examined were 0.33 mg/kg and 1.0 mg/kg. Mice with advanced tumor burden were sacrificed upon showing symptoms of hind limb paralysis, cranial swelling, and/or moribundity. As shown in FIG. 11, the of hMEM102-MDpr-PEG(12)-gluc-MMAE (5088) ADC produced the most potent antitumor response, 6/8 complete responses at 0.33 mg/kg and 7/8 complete responses at 1.0 mg/kg. Non-binding control ADC dosed mice were all sacrificed due to disease by day-60 of the study.

Example 6: Effector Function

Methods For WIL2-S target cells, antibody dependent cellular cytotoxicity (ADCC) was measured through chromium-51 release using purified natural killer (NK) cells combined with antibody coated CD48-positive target cells. WIL2-S tumor cells were labeled with chromium-51 and pre-incubated for 30 minutes with antibody (0.1 ng/mL-10 μm/mL). Target cells were then combined with NK effector cells (effector/target ratio 10:1) and incubated an additional 4 hours at 37° C., 5% CO2. Chromium-51 in the supernatant was then quantified on a Perkin Elmer TopCount plate reader. ADCC activity is measured as a percentage of maximum lysis relative to 1% Triton X-100 treated control target cells. ADCC was assayed for normal human resting T cells (All Cells) using the same NK cell effector ratio and anti-CD48 antibody or ADC titration range described above; however, the PKH2 green fluorescent cell linker kit (Sigma) was used to label the cell membrane (not chromium-51). 7-AAD dye was used to measure T cell viability by flow cytometry, using the LSRII flow cytometer (Becton Dickinson).

Complement dependent cytotoxicity was measured by incubating normal human T cells or WIL2-S tumor cells with serially diluted antibody (0.02-50 μm/mL) in RPMI 1640 culture media containing 10% heat-inactivated human AB serum and 5 μM Sytox Green fluorescent dye. Cells were then incubated for 2 hours at 37° C., 5% CO$_2$. Fluorescence from lysed cells was measured on an Envision plate reader. Maximum specific lysis of target cells was calculated as a percentage of 1% Triton X-100 treated control cells.

Antibody dependent cellular phagocytosis was measured using monocyte derived macrophages as effector cells and PKH26 red fluorescent dye labeled normal human T cells (All Cells), WIL2-S, or Raji tumor cells. Target cells were pre-incubated with serially diluted antibody (0.2 ng/mL-2 µm/mL) for 30 minutes, and then washed twice with phosphate buffered saline. Macrophages were added to target cells at a 4:1 ratio in RPMI 1640 culture media containing 10% low IgG fetal bovine serum and incubated for 2 hours at 37° C., 5% $CO_2$. Macrophages were then labeled with Alexa Fluor®-488 conjugated mouse anti-human CD11b antibody. Tumor cell positive macrophages were detected as events showing green and red dual fluorescence on a FACSCalibur flow cytometer. Maximum specific phagocytic activity is presented as the percentage of tumor positive macrophages after subtraction of non-binding isotype control background activity.

Results:

ADCC activity of the unconjugated hMEM102 antibody and the hMEM102-MDpr-PEG(12)-gluc-MMAE (5088) ADC were assessed and compared to ADCC activity of CAMPATH® (Alemtuzumab, anti-CD52 antibody) and rituximab (anti-CD20 antibody). As shown in Table 3, humanized MEM102-HALA antibody has moderate ADCC activity against normal resting T cells and WIL2-S tumor cell line. ADCC activity is significantly reduced upon 5088 conjugation, resulting in 2.7-fold less ADCC activity in T cells compared to the naked antibody.

TABLE 3

ADCC

| | | | | Maximum % Specific Cell Lysis | | | |
|---|---|---|---|---|---|---|---|
| Cell Type | CD48 Receptor # | CD52 Receptor # | CD20 Receptor # | hMEM102-- HALA | hMEM102- HALA- 5088 | Campath (CD52) | Rituximab (CD20) |
| Normal Human T cells (n = 2) | 38,900 | 115,200 | | 65 ± 3.1 | 24 ± 4.4 | 60 ± 3.5 | |
| WIL2-5 (n = 2) | 359,558 | 34,200 | 502,700 | 43 ± 0.6 | 17 ± 1.0 | | 42 ± 6.0 |

CDC activity results are shown in Table 4. Neither the unconjugated hMEM102 antibody nor the hMEM102-MDpr-PEG(12)-gluc-MMAE (5088) ADC exhibited CDC activity against normal resting T cells and WIL2-S tumor cells. Both alemtuzumab and rituximab exhibited substantial CDC activity against the target cells.

TABLE 4

CDC

| | | | | Maximum % Specific Cell Lysis | | | |
|---|---|---|---|---|---|---|---|
| Cell Type | CD48 Receptor # | CD52 Receptor # | CD20 Receptor # | hMEM102-- HALA | hMEM102- HALA- 5088 | Campath (CD52) | Rituximab (CD20) |
| Normal Human T cells (n = 2) | 38,900 | 115,200 | | 2.4 ± 0.6 | 1.9 ± 2.7 | 108 ± 5.2 | |
| WIL2-5 (n = 2) | 359,558 | 34,200 | 502,700 | 0.9 ± 0.2 | 1.4 ± 0.9 | | 66 ± 1.4 |

ADCP results are shown in Table 5. Both the unconjugated hMEM102 antibody and the hMEM102-MDpr-PEG(12)-gluc-MMAE (5088) ADC exhibited moderate ADCP activity against normal resting T cells or WIL2-S and Raji tumor cell lines, consistent with levels observed with Campath and Rituximab.

TABLE 5

| | | | | Maximum % Specific Cell Lysis | | | |
|---|---|---|---|---|---|---|---|
| Cell Type | CD48 Receptor # | CD52 Receptor # | CD20 Receptor # | hMEM102--HALA | hMEM102-HALA-5088 | Campath (CD52) | Rituximab (CD20) |
| Normal Human T cells (n = 2) | 38,900 | 115,200 | | 56 | 54 | 57 | |
| WIL2-S (n = 2) | 359,558 | 34,200 | 502,700 | 62 | 60 | | 56 |
| Raji | 249,023 (24%) | 29,200 | 394,100 | 37 | 34 | | 57 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING hMEM102 HA - Heavy chain variable region
SEQ ID NO: 1
QVQLVQSGSELKKPGASVKVSCKASGYTFTDFGMNWVRQAPGQGLEWMG
WINTFTGEPSYGNVFKGRFVFSLDTSVSTAYLQISSLKAEDTAVYYCAR
RHGNGNVFDSWGQGTLVTVSS, hMEM102 LA - Light chain variable region
SEQ ID NO: 2
EIVLTQSPDFQSVTPKEKVTITCRASQSIGSNIHWYQQKPDQSPKLLIK
YTSESISGVPSRFSGSGSGTDFTLTINSLEAEDAATYYCQQSNSWPLTF
GGGTKVEIKR, heavy chain CDR1
SEQ ID NO: 3
DFGMN, heavy chain CDR2
SEQ ID NO: 4
WINTFTGEPSYGNVFKG, heavy chain CDR3
SEQ ID NO: 5
RHGNGNVFDS, light chain CDR1
SEQ ID NO: 6
RASQSIGSNIH, light chain CDR2
SEQ ID NO: 7
YTSESIS, light chain CDR3
SEQ ID NO: 8
QQSNSWPLT, hMEM102 HA H-chain G1
SEQ ID NO: 9
QVQLVQSGSELKKPGASVKVSCKASGYTFTDFGMNWVRQAPGQGLEWMG
WINTFTGEPSYGNVFKGRFVFSLDTSVSTAYLQISSLKAEDTAVYYCAR
RHGNGNVFDSWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPGK, hMEM102 LA L-chain
SEQ ID NO: 10
EIVLTQSPDFQSVTPKEKVTITCRASQSIGSNIHWYQQKPDQSPKLLIK
YTSESISGVPSRFSGSGSGTDFTLTINSLEAEDAATYYCQQSNSWPLTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC, Naturally occurring heavy chain constant region
SEQ ID NO: 11
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG, Light chain constant region
SEQ ID NO: 12
TVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVT
KSFNRGEC,

What is claimed is:

1. A chimeric or humanized antibody that specifically binds to the human CD48 protein, wherein the antibody comprises heavy chain CDR sequences of SEQ ID NOs:3-5 and light chain CDR sequences of SEQ ID NOs:6-8, and wherein the antibody exhibits higher binding affinity to the human CD48 protein, as compared to a murine antibody that specifically binds to the human CD48 protein and comprises heavy chain CDR sequences of SEQ ID NOs:3-5 and light chain CDR sequences of SEQ ID NOs:6-8.

2. The antibody of claim 1, wherein the chimeric or humanized antibody exhibits at least 2-fold higher binding affinity for the human CD48 protein, as compared to the murine antibody.

3. The antibody of claim 1, wherein the antibody is a humanized antibody.

4. The antibody of claim 1, wherein the antibody comprises a heavy chain variable region having at least 90% identity to SEQ ID NO:1.

5. The antibody of claim 1, wherein the antibody comprises a light chain variable region having at least 90% identity to SEQ ID NO:2.

6. The antibody of claim 1, wherein the antibody comprises a heavy chain variable region having at least 95% identity to SEQ ID NO:1.

7. The antibody of claim 1, wherein the antibody comprises a light chain variable region having at least 95% identity to SEQ ID NO:2.

8. The antibody of claim 1, wherein the antibody comprises a heavy chain variable region of SEQ ID NO:1.

9. The antibody of claim 1, wherein the antibody comprises a light chain variable region of SEQ ID NO:2.

10. The antibody of claim 1, wherein the antibody comprises a heavy chain variable region having at least 90% identity to SEQ ID NO:1 and a light chain variable region having at least 90% identity to SEQ ID NO:2.

11. The antibody of claim 1, wherein the antibody comprises a heavy chain variable region having at least 95% identity to SEQ ID NO:1 and a light chain variable region having at least 95% identity to SEQ ID NO:2.

12. The antibody of claim 1, wherein the antibody comprises a heavy chain variable region of SEQ ID NO:1 and a light chain variable region of SEQ ID NO:2.

13. A composition comprising a population of the antibody of claim 1 or a pharmaceutically acceptable salt thereof.

14. A method of treating a patient having a cancer that expresses CD48, comprising administering to the patient an effective regimen of the composition of claim 13.

15. The method of claim 14, wherein the cancer is selected from the group consisting of multiple myeloma, B cell malignancies and acute myelogenous leukemia.

16. The method of claim 14, wherein the cancer is multiple myeloma.

17. An antibody-drug conjugate comprising a chimeric or humanized antibody that specifically binds to the human CD48 protein and a drug-linker, wherein the antibody comprises heavy chain CDR sequences of SEQ ID NOs:3-5 and light chain CDR sequences of SEQ ID NOs:6-8, wherein the antibody exhibits higher binding affinity to the human CD48 protein, as compared to a murine antibody that specifically binds to the human CD48 protein and comprises heavy chain CDR sequences of SEQ ID NOs:3-5 and light chain CDR sequences of SEQ ID NOs:6-8, and wherein the antibody is conjugated to the drug-linker comprising a cytotoxic drug attached to a linker.

18. The antibody-drug conjugate of claim 17, wherein the chimeric or humanized antibody exhibits at least 2-fold higher binding affinity for the human CD48 protein, as compared to the murine antibody.

19. The antibody-drug conjugate of claim 17, wherein the antibody is a humanized antibody.

20. The antibody-drug conjugate of claim 17, wherein the antibody comprises a heavy chain variable region having at least 90% identity to SEQ ID NO:1.

21. The antibody-drug conjugate of claim 17, wherein the antibody comprises a light chain variable region having at least 90% identity to SEQ ID NO:2.

22. The antibody-drug conjugate of claim 17, wherein the antibody comprises a heavy chain variable region having at least 95% identity to SEQ ID NO:1.

23. The antibody-drug conjugate of claim 17, wherein the antibody comprises a light chain variable region having at least 95% identity to SEQ ID NO:2.

24. The antibody-drug conjugate of claim 17, wherein the antibody comprises a heavy chain variable region of SEQ ID NO:1.

25. The antibody-drug conjugate of claim 17, wherein the antibody comprises a light chain variable region of SEQ ID NO:2.

26. The antibody-drug conjugate of claim 17, wherein the antibody comprises a heavy chain variable region having at least 90% identity to SEQ ID NO:1 and a light chain variable region having at least 90% identity to SEQ ID NO:2.

27. The antibody-drug conjugate of claim 17, wherein the antibody comprises a heavy chain variable region having at least 95% identity to SEQ ID NO:1 and a light chain variable region having at least 95% identity to SEQ ID NO:2.

28. The antibody-drug conjugate of claim 17, wherein the antibody comprises a heavy chain variable region of SEQ ID NO:1 and a light chain variable region of SEQ ID NO:2.

29. The antibody-drug conjugate of claim 17 wherein the drug-linker has the formula:

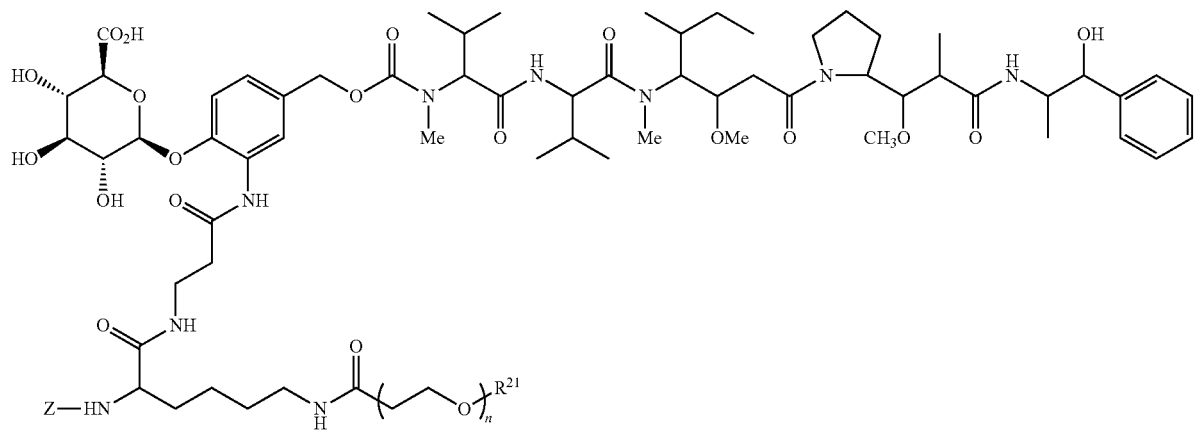

or a pharmaceutically acceptable salt thereof wherein Z represents an organic moiety having a reactive site capable of reacting with a functional group on the antibody to form a covalent attachment thereto, n ranges from 8 to 36, and $R^{21}$ is a capping unit for the polyethylene glycol moiety.

30. The antibody-drug conjugate of claim 29 wherein n ranges from 8 to 14.

31. The antibody-drug conjugate of claim 29 wherein $R^{21}$ is —$CH_3$ or —$CH_2CH_2CO_2H$.

32. The antibody-drug conjugate of claim 29 wherein n is 12.

33. The antibody-drug conjugate of claim 29 wherein n is 12 and $R^{21}$ is —$CH_3$.

34. The antibody-drug conjugate of claim 29 wherein attachment of the drug-linker to the antibody is via the cysteine residues of interchain disulfide bonds of the antibody.

35. The antibody-drug conjugate of claim 17 wherein the drug-linker has the formula:

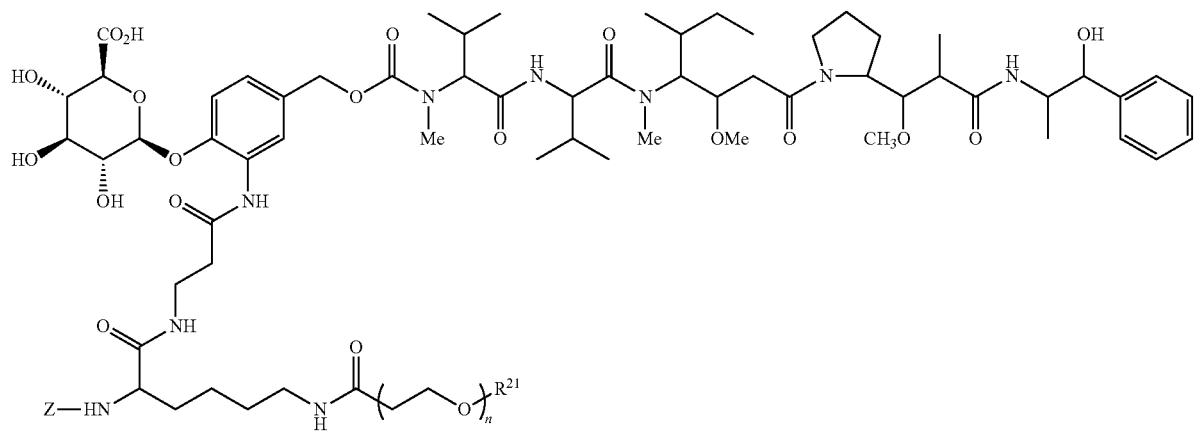

or a pharmaceutically acceptable salt thereof wherein, n ranges from 8 to 36, $R^{PR}$ is hydrogen or a protecting group, and $R^{21}$ is a capping unit for the polyethylene glycol moiety.

36. The antibody-drug conjugate of claim 35, wherein n is 12, $R^{PR}$ is a hydrogen, and $R^{21}$ is —$CH_3$.

37. The antibody-drug conjugate of claim 17 having the formula:

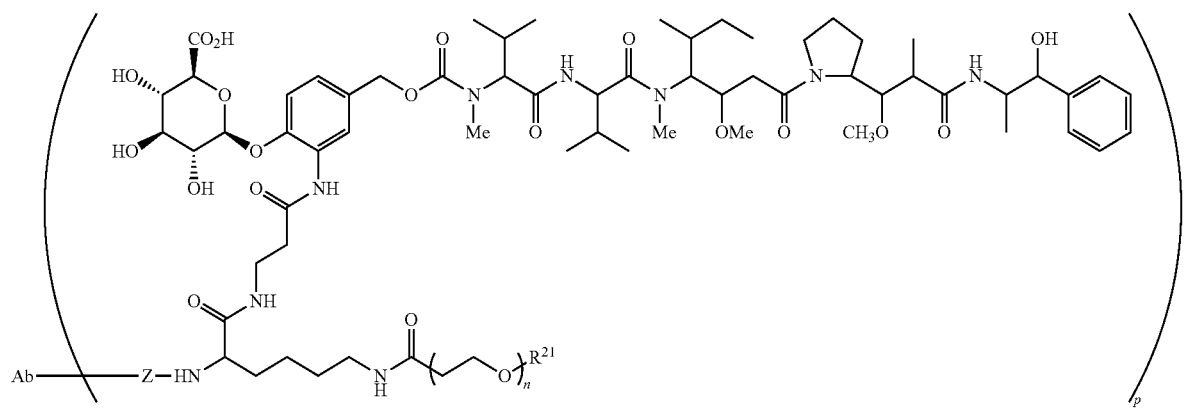

or a pharmaceutically acceptable salt thereof wherein: Ab represents the antibody, Z represents an organic moiety having a reactive site capable of reacting with a functional group on the antibody to form a covalent attachment thereto, n ranges from 8 to 36, $R^{21}$ is a capping unit for the polyethylene glycol moiety, and p represents the number of the drug-linkers attached to the antibody and is from 1 to 16.

38. The antibody-drug conjugate of claim 37 wherein n ranges from 8 to 14.

39. The antibody-drug conjugate of claim 37 wherein $R^{21}$ is —$CH_3$ or —$CH_2CH_2CO_2H$.

40. The antibody-drug conjugate of claim 37 wherein n is 12.

41. The antibody-drug conjugate of claim 37 wherein n is 12 and $R^{21}$ is —$CH_3$.

42. A pharmaceutical composition comprising a population of the antibody-drug conjugate of claim 37 wherein p is 8.

43. An antibody-drug conjugate having the formula:

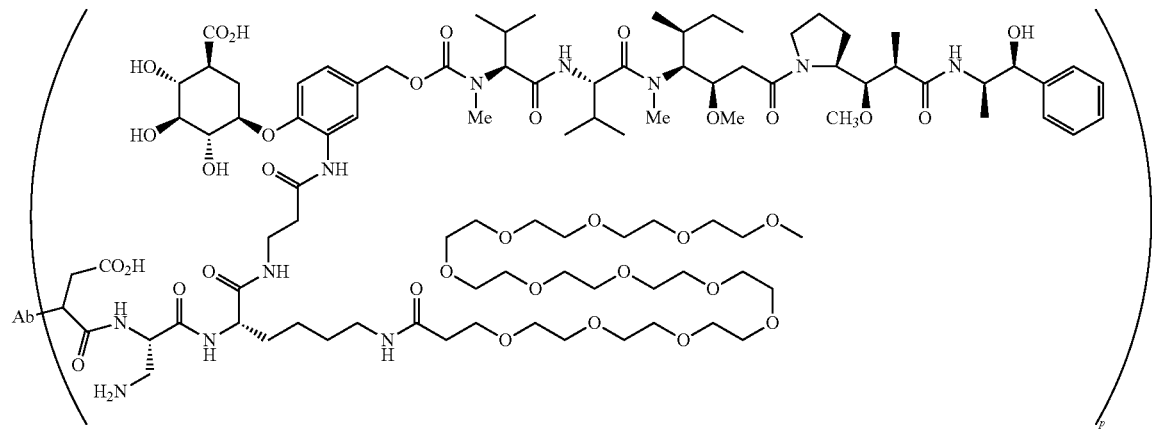

or

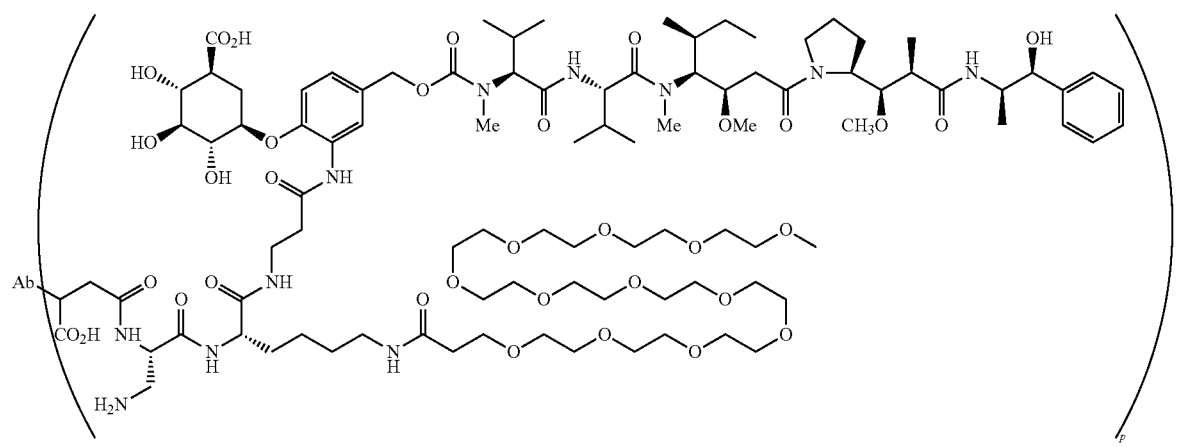

wherein Ab is a chimeric or humanized antibody that specifically binds to the human CD48 protein, wherein the antibody comprises a heavy chain variable region of SEQ ID NO: 1 and a light chain variable region of SEQ ID NO: 2, and wherein p represents the number of the drug-linkers attached to the antibody and is 8.

44. A method of treating a patient having a cancer that expresses CD48, comprising administering to the patient an effective regimen of the antibody-drug conjugate of claim 17.

45. The method of claim 44, wherein the cancer is selected from the group consisting of multiple myeloma, B cell malignancies and acute myelogenous leukemia.

46. The method of claim 44, wherein the cancer is multiple myeloma.

47. An isolated nucleic acid comprising a sequence encoding a heavy chain variable region comprising the amino acid sequence of SEQ ID NO: 1 and a light chain variable region comprising the amino acid sequence of SEQ ID NO: 2.

48. An isolated vector comprising the nucleic acid of claim 47.

49. An isolated host cell comprising the vector of claim 48.

50. The host cell of claim 49, wherein the host cell is a CHO cell.

51. A method of making an anti-CD48 antibody or antigen binding fragment thereof, wherein the method comprises:
 a) culturing the host cell of claim 49 under conditions suitable for expression of the polynucleotide encoding the antibody or antigen binding fragment thereof; and
 b) isolating the antibody or antigen binding fragment thereof.

52. The method of claim 51, wherein the host cell is a CHO cell.

53. A method of making an anti-CD48 antibody-drug conjugate, wherein the method comprises:
 a) culturing the host cell of claim 49 under conditions suitable for expression of the polynucleotide encoding the antibody or antigen binding fragment thereof;
 b) isolating the antibody or antigen binding fragment thereof; and
 c) conjugating a cytotoxic agent to the antibody or antigen binding fragment thereof.

54. The method of claim 53, wherein the host cell is a CHO cell.

55. The method of claim 53, wherein the cytotoxic agent is has the formula

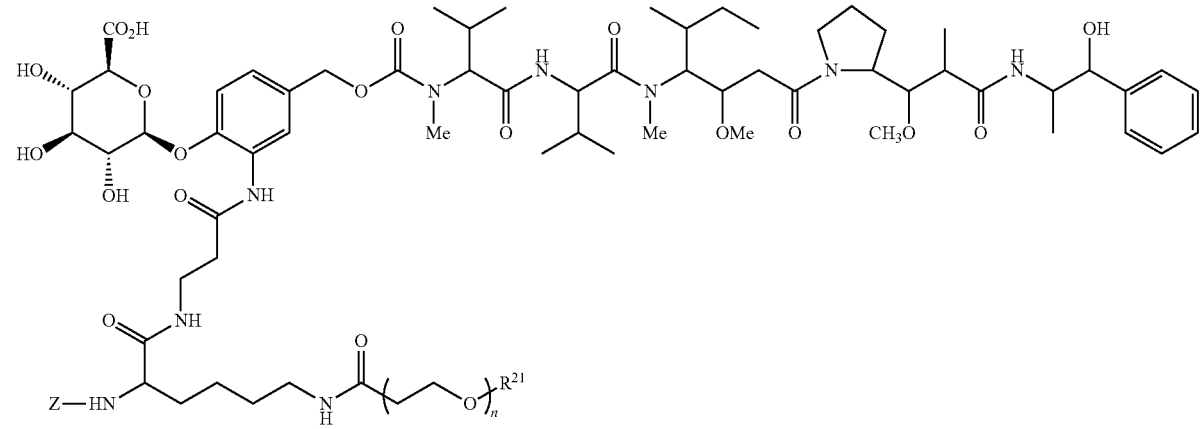

or a pharmaceutically acceptable salt thereof wherein Z represents an organic moiety having a reactive site capable of reacting with a functional group on the antibody to form a covalent attachment thereto, n ranges from 8 to 36, and R21 is a capping unit for the polyethylene glycol moiety.

* * * * *

SEQUENCE LISTING

<160> NUMBER OF SEQ ID NOS: 12

<210> SEQ ID NO 1
<211> LENGTH: 119
<212> TYPE: PRT
<213> ORGANISM: Artificial
<220> FEATURE:
<223> OTHER INFORMATION: hMEM102 HA - Heavy chain variable region

<400> SEQUENCE: 1

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Phe
            20                  25                  30

Gly Met Asn Trp Val Arg Gln Ala Pro Gly Gln Gly Leu Glu Trp Met
        35                  40                  45

Gly Trp Ile Asn Thr Phe Thr Gly Glu Pro Ser Tyr Gly Asn Val Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg His Gly Asn Gly Asn Val Phe Asp Ser Trp Gly Gln Gly
            100                 105                 110

Thr Leu Val Thr Val Ser Ser
        115
```

<210> SEQ ID NO 2
<211> LENGTH: 108
<212> TYPE: PRT
<213> ORGANISM: Artificial
<220> FEATURE:
<223> OTHER INFORMATION: hMEM102 LA - Light chain variable region

<400> SEQUENCE: 2

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Asn
            20                  25                  30

Ile His Trp Tyr Gln Gln Lys Pro Asp Gln Ser Pro Lys Leu Leu Ile
        35                  40                  45

Lys Tyr Thr Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Leu
                85                  90                  95

Thr Phe Gly Gly Gly Thr Lys Val Glu Ile Lys Arg
            100                 105
```

<210> SEQ ID NO 3
<211> LENGTH: 5
<212> TYPE: PRT
<213> ORGANISM: Artificial
<220> FEATURE:
<223> OTHER INFORMATION: heavy chain CDR1

<400> SEQUENCE: 3

```
Asp Phe Gly Met Asn
1               5
```

```
<210> SEQ ID NO 4
<211> LENGTH: 17
<212> TYPE: PRT
<213> ORGANISM: Artificial
<220> FEATURE:
<223> OTHER INFORMATION: heavy chain CDR2

<400> SEQUENCE: 4

Trp Ile Asn Thr Phe Thr Gly Glu Pro Ser Tyr Gly Asn Val Phe Lys
1               5                   10                  15
Gly

<210> SEQ ID NO 5
<211> LENGTH: 10
<212> TYPE: PRT
<213> ORGANISM: Artificial
<220> FEATURE:
<223> OTHER INFORMATION: heavy chain CDR3

<400> SEQUENCE: 5

Arg His Gly Asn Gly Asn Val Phe Asp Ser
1               5                   10

<210> SEQ ID NO 6
<211> LENGTH: 11
<212> TYPE: PRT
<213> ORGANISM: Artificial
<220> FEATURE:
<223> OTHER INFORMATION: light chain CDR1

<400> SEQUENCE: 6

Arg Ala Ser Gln Ser Ile Gly Ser Asn Ile His
1               5                   10

<210> SEQ ID NO 7
<211> LENGTH: 7
<212> TYPE: PRT
<213> ORGANISM: Artificial
<220> FEATURE:
<223> OTHER INFORMATION: light chain CDR2

<400> SEQUENCE: 7

Tyr Thr Ser Glu Ser Ile Ser
1               5

<210> SEQ ID NO 8
<211> LENGTH: 9
<212> TYPE: PRT
<213> ORGANISM: Artificial
<220> FEATURE:
<223> OTHER INFORMATION: light chain CDR3

<400> SEQUENCE: 8

Gln Gln Ser Asn Ser Trp Pro Leu Thr
1               5

<210> SEQ ID NO 9
<211> LENGTH: 449
<212> TYPE: PRT
<213> ORGANISM: Artificial
<220> FEATURE:
<223> OTHER INFORMATION: hMEM102 HA H-chain G1

<400> SEQUENCE: 9

Gln Val Gln Leu Val Gln Ser Gly Ser Glu Leu Lys Lys Pro Gly Ala
```

-continued

```
1               5                   10                  15
Ser Val Lys Val Ser Cys Lys Ala Ser Gly Tyr Thr Phe Thr Asp Phe
                20                  25                  30

Gly Met Asn Trp Val Arg Gln Ala Pro Gly Gln Gly Leu Glu Trp Met
                35                  40                  45

Gly Trp Ile Asn Thr Phe Thr Gly Glu Pro Ser Tyr Gly Asn Val Phe
            50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg His Gly Asn Gly Asn Val Phe Asp Ser Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
        435                 440                 445

Lys

<210> SEQ ID NO 10
<211> LENGTH: 214
<212> TYPE: PRT
<213> ORGANISM: Artificial
<220> FEATURE:
<223> OTHER INFORMATION: hMEM102 LA L-chain

<400> SEQUENCE: 10

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Asn
            20                  25                  30

Ile His Trp Tyr Gln Gln Lys Pro Asp Gln Ser Pro Lys Leu Leu Ile
        35                  40                  45

Lys Tyr Thr Ser Glu Ser Ile Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 329
<212> TYPE: PRT
<213> ORGANISM: Artificial
<220> FEATURE:
<223> OTHER INFORMATION: Naturally occurring heavy chain constant region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 12
<211> LENGTH: 106
<212> TYPE: PRT
<213> ORGANISM: Artificial
<220> FEATURE:
<223> OTHER INFORMATION: Light chain constant region

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

```
Val Thr Lys Ser Phe Asn Arg Gly Glu Cys
            100                     105
```